US012582394B2

(12) United States Patent
Szivek et al.

(10) Patent No.: US 12,582,394 B2
(45) Date of Patent: Mar. 24, 2026

(54) IMPLANTABLE MINIATURIZED AND SOFT WIRELESS SENSING DEVICE TO MONITOR TISSUE AND BONE DEFORMATION

(71) Applicant: ARIZONA BOARD OF REGENTS ON BEHALF OF THE UNIVERSITY OF ARIZONA, Tucson, AZ (US)

(72) Inventors: John Szivek, Tucson, AZ (US); Philipp Gutruf, Tucson, AZ (US); David Stephen Margolis, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 449 days.

(21) Appl. No.: 18/042,088

(22) PCT Filed: Aug. 16, 2021

(86) PCT No.: PCT/US2021/046173
§ 371 (c)(1),
(2) Date: Feb. 17, 2023

(87) PCT Pub. No.: WO2022/040102
PCT Pub. Date: Feb. 24, 2022

(65) Prior Publication Data
US 2023/0309985 A1      Oct. 5, 2023

Related U.S. Application Data

(60) Provisional application No. 63/066,781, filed on Aug. 17, 2020.

(51) Int. Cl.
A61B 17/04      (2006.01)
A61F 2/28      (2006.01)
A61F 2/30      (2006.01)

(52) U.S. Cl.
CPC ............ *A61B 17/0401* (2013.01); *A61F 2/28* (2013.01); *A61F 2002/30677* (2013.01)

(58) Field of Classification Search
CPC ........ A61B 17/0401; A61B 2560/0219; A61B 2562/0261; A61B 5/4504; A61B 5/6878;
(Continued)

(56) References Cited

U.S. PATENT DOCUMENTS 12,251,201 B2 *  3/2025  Poltorak .............. A61B 5/0022
12,376,757 B2 *  8/2025  Toth ..................... A61B 5/6885
(Continued)

FOREIGN PATENT DOCUMENTS

CA      2620247 A1 *  3/2007  ............. A61B 17/72
CA      3225445 A1 *  12/2014  ........... A61B 5/4851
(Continued)

*Primary Examiner* — Jeffrey G. Hoekstra
(74) *Attorney, Agent, or Firm* — NGUYEN TARBET IP LAW

(57) ABSTRACT

The present invention features a sensor implant that can adhere to bone. The sensing device is capable of sensing bone strains and reporting them as well as loads passing through bone for extended periods of time. The sensor implant can also be used to monitor bone growth for bone segmental repair of long bones or to monitor changes in bone characteristics of patients with osteoporosis. The present technology has the potential to give physicians the ability to predict when a patient with osteoporosis has an impending fracture and thus be able to intervene and prevent further damage.

9 Claims, 15 Drawing Sheets

(58) Field of Classification Search
CPC .. A61F 2/28; A61F 2002/30677; G01L 1/225;
G01L 1/26
See application file for complete search history.

(56) References Cited

U.S. PATENT DOCUMENTS

| | | | | |
|---|---|---|---|---|
| 2006/0047283 A1* | 3/2006 | Evans | .................. | A61B 5/6846 |
| | | | | 623/20.2 |
| 2012/0123221 A1* | 5/2012 | Windolf | ............... | A61B 5/0031 |
| | | | | 600/300 |
| 2015/0265213 A1* | 9/2015 | Munro | ................. | A61B 5/4566 |
| | | | | 600/587 |
| 2019/0134419 A1* | 5/2019 | Bourke, Jr. | ............. | A61P 37/00 |

FOREIGN PATENT DOCUMENTS

| | | | | | |
|---|---|---|---|---|---|
| CA | 3031245 C | * | 9/2023 | ........... | A61B 5/0031 |
| WO | WO-0215769 A2 | * | 2/2002 | ............. | A61F 2/442 |
| WO | WO-2010028077 A1 | * | 3/2010 | ............. | G01L 1/144 |
| WO | WO-2018009905 A2 | * | 1/2018 | ........... | A61N 1/3787 |

* cited by examiner

FIG. 2A          FIG. 2B
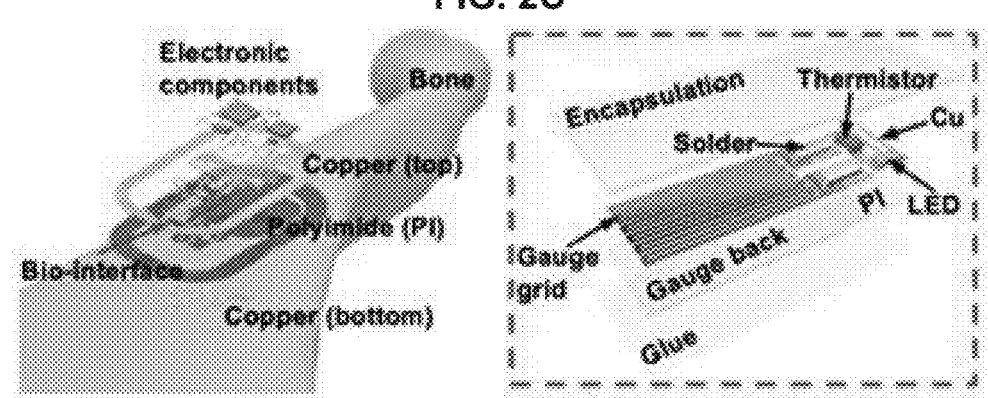
FIG. 2C
FIG. 2D          FIG. 2F
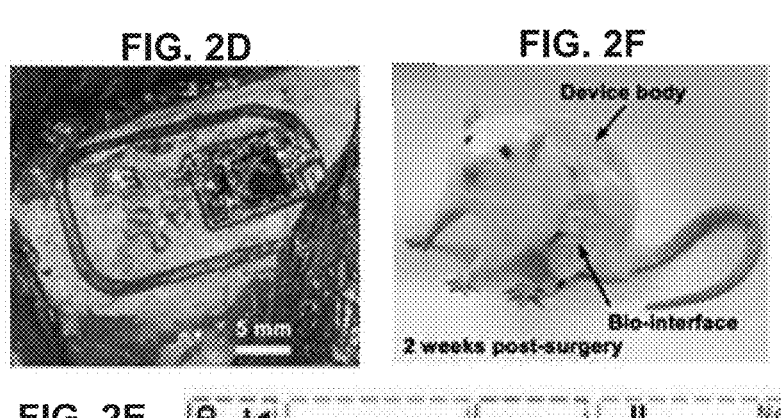
FIG. 2E
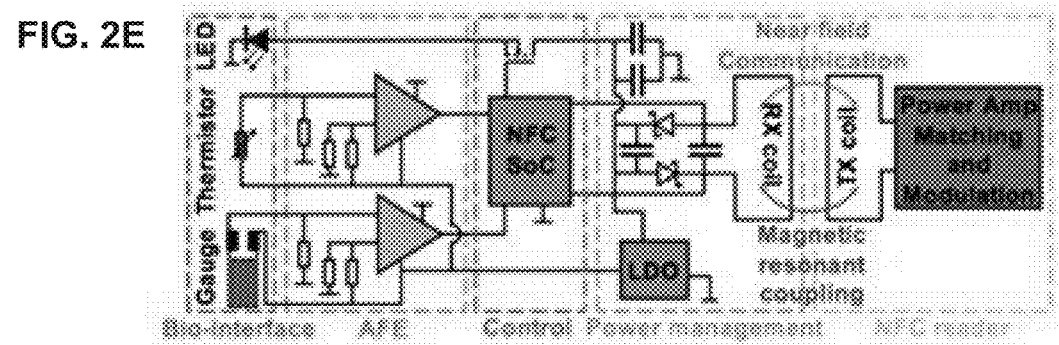

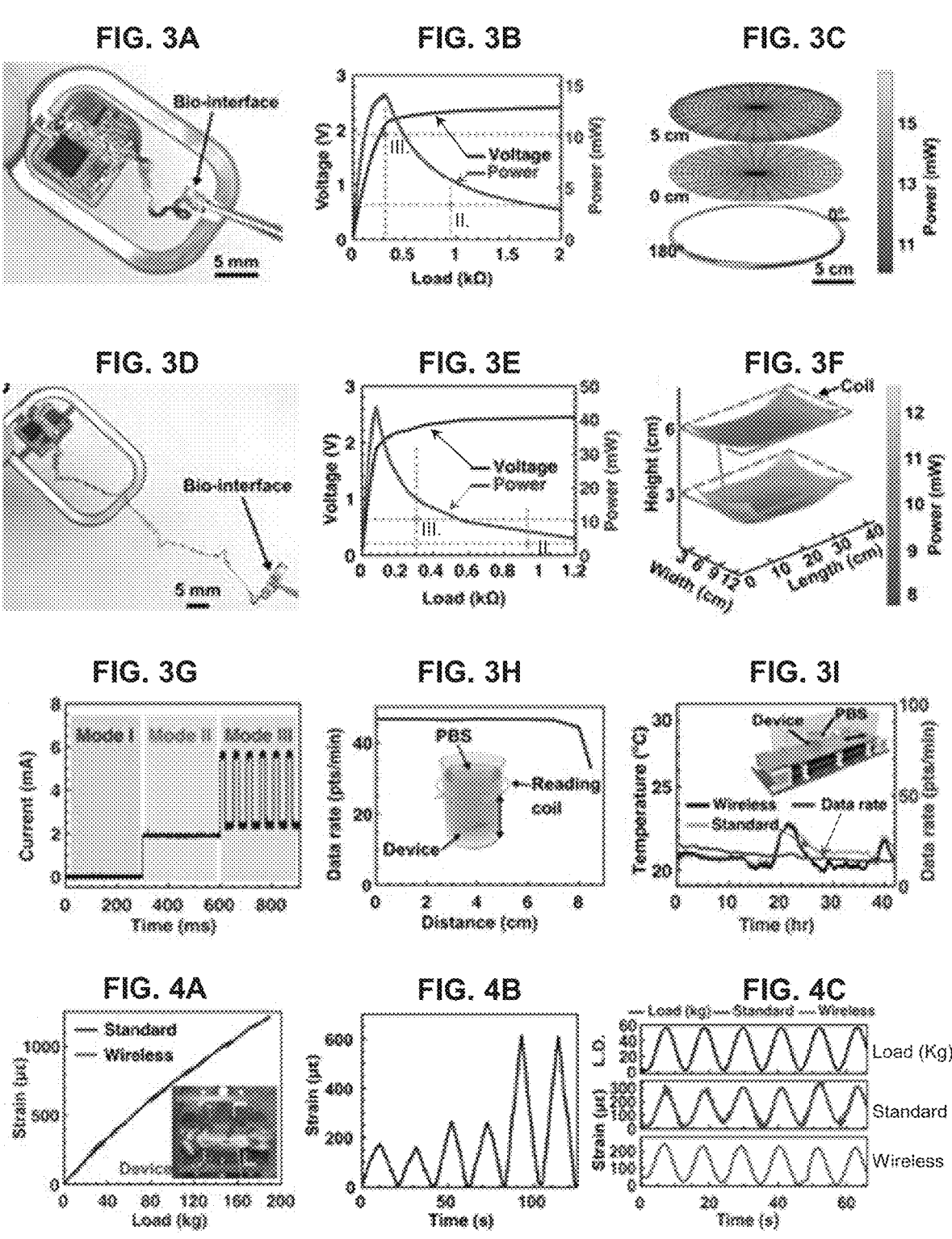

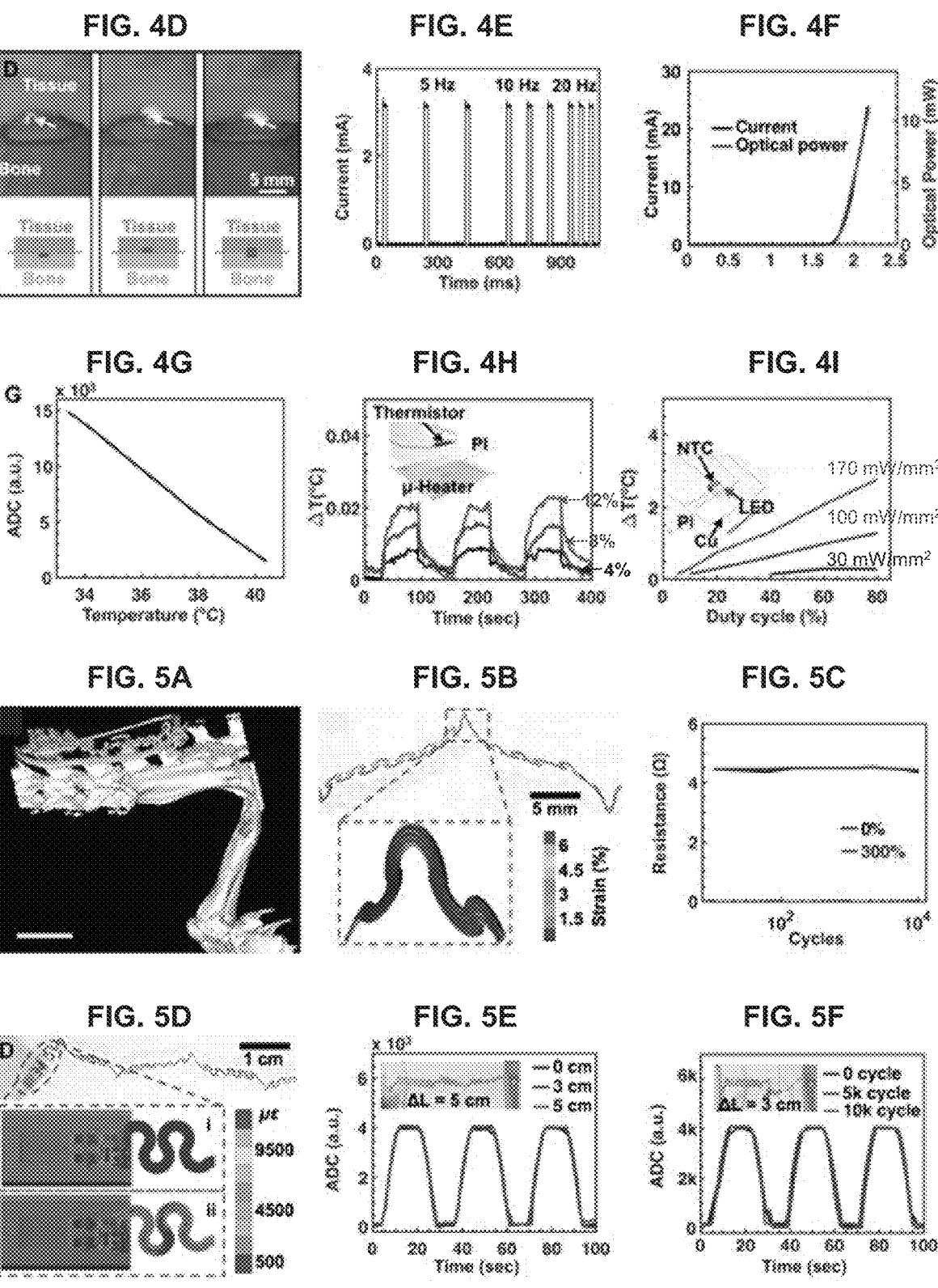

FIG. 7D          FIG. 7E          FIG. 7F
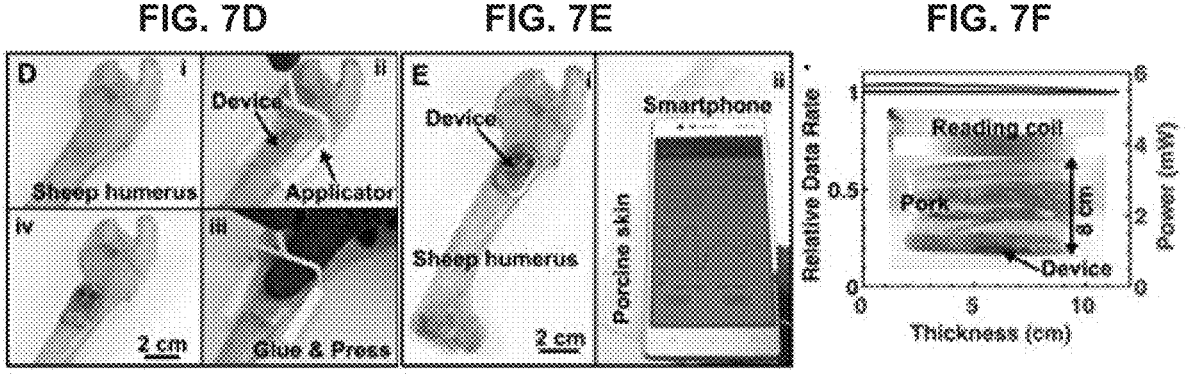
FIG. 8A          FIG. 8B          FIG. 8C
FIG. 8D
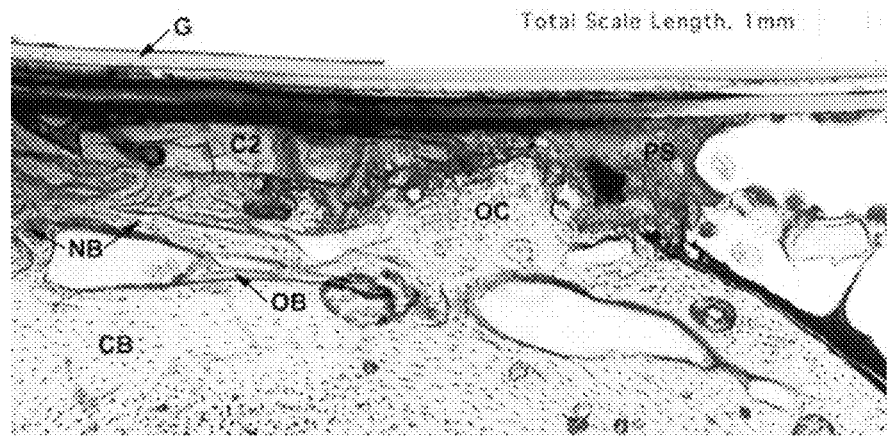

| C1 | 2.2 µF | R12 | 150Ωk |
| --- | --- | --- | --- |
| C2-C5 | 100 nF | NTC | NTCG064EF104FTBX |
| C6, C7 | 10 nF | LED | APG0603SEC-E-TT |
| C8-C12 | 1 µF | Strain gauge | N2A-06-S5182N-10C/E4 |
| C13-C20 | 22 µF | U1 | LDO, 1.8V, TCR2DG18 |
| R1-R4 | 1Ωk | U2 | Instrumentation amplifier, AD8235 |
| R5-R8 | 47Ωk | U3 | NFC SoC, RF430RFL152H |
| R9, R10 | 10Ωk | U4 | ATTiny 13A |
| R11 | 500Ωk | U5 | MOSFET, PMZ130UNE |

FIG. 16B          FIG. 16C

FIG. 17A
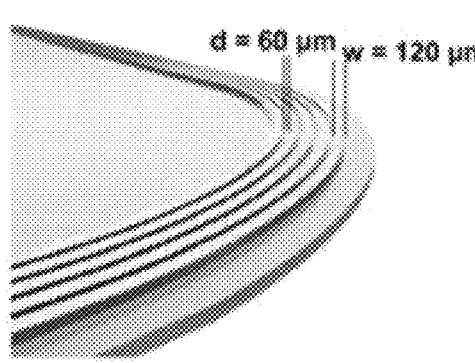
FIG. 17B
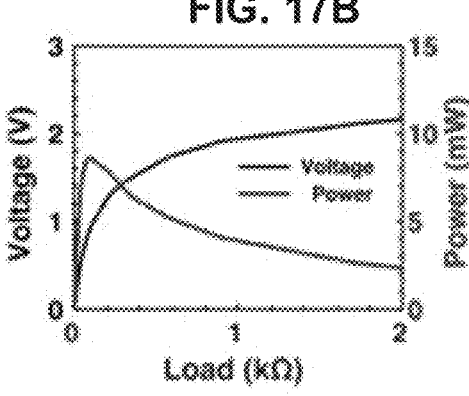
FIG. 17C
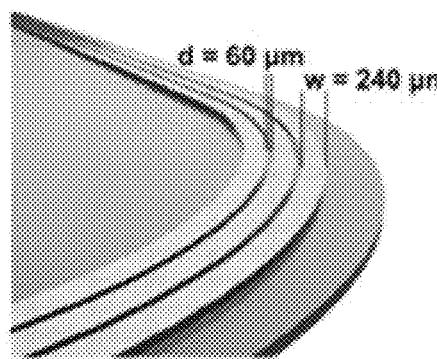
FIG. 17D
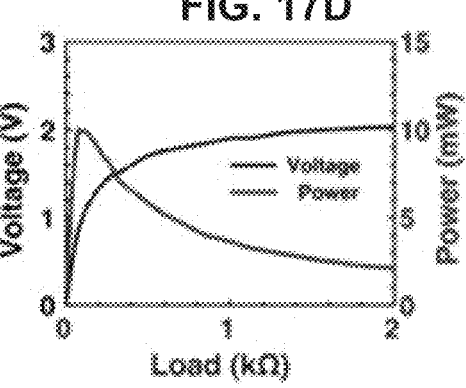
FIG. 17E
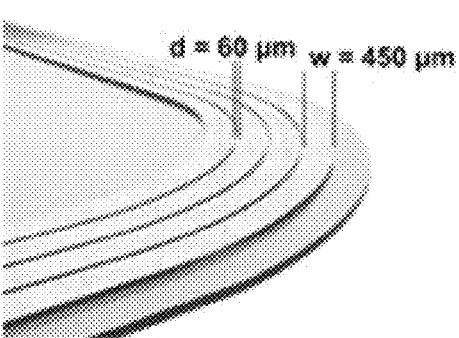
FIG. 17F
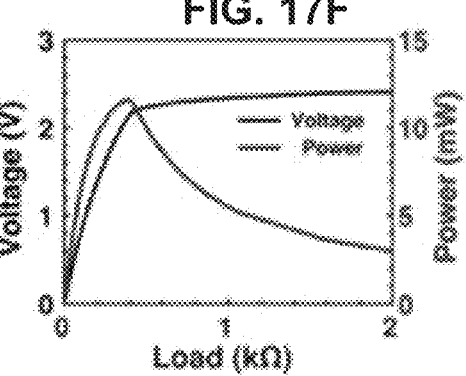
FIG. 17G
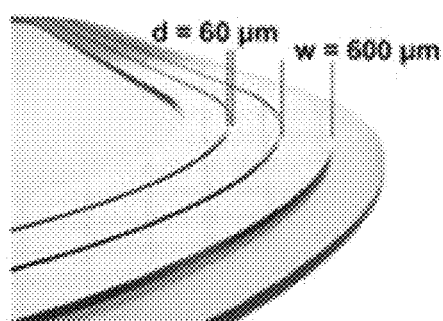
FIG. 17H
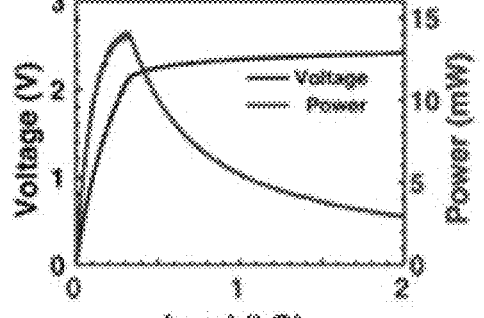

FIG. 22A
FIG. 22B
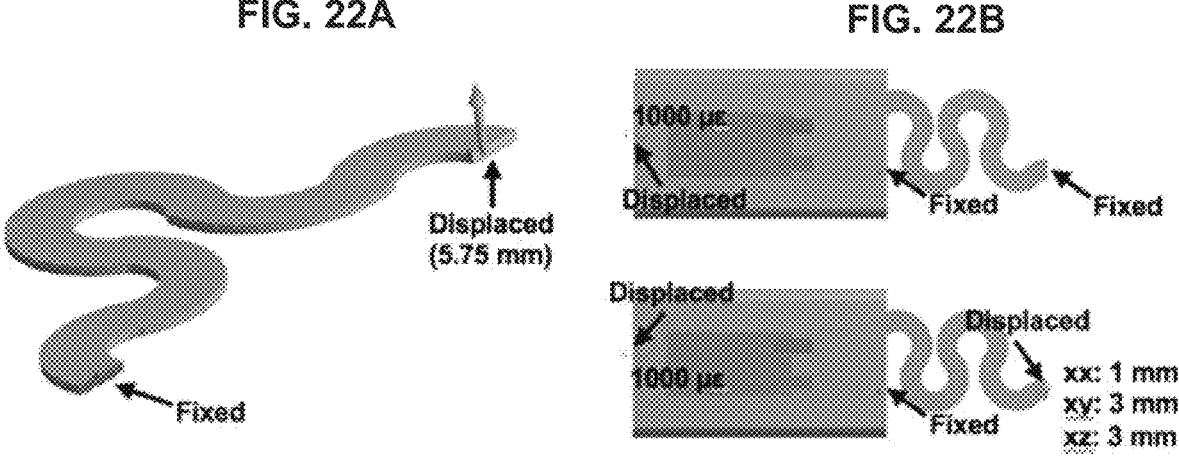
FIG. 23
FIG. 24
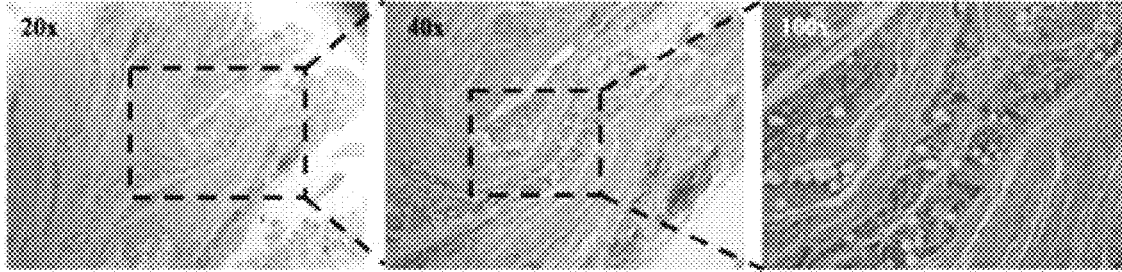

IMPLANTABLE MINIATURIZED AND SOFT WIRELESS SENSING DEVICE TO MONITOR TISSUE AND BONE DEFORMATION

CROSS-REFERENCES TO RELATED APPLICATIONS

This application claims benefit of U.S. Provisional Application No. 63/066,781 filed Aug. 17, 2020, the specification of which is incorporated herein in their entirety by reference.

FIELD OF THE INVENTION

The present invention features a strain sensing device, more particularly a sensing device that incorporates the sensor, amplification, preprocessing, and energy harvesting for battery free operation and signal transmission in a single device for use by any patient.

BACKGROUND OF THE INVENTION

Continuous recording of biosignals with high fidelity has been widely recognized to play a key role in modern exploratory research, diagnostics and therapeutics. Specifically, with the emergence of computational tools such as neural networks, artificial intelligence and machine learning that can help to analyze large datasets, continuous high-quality data streams will enable the development of diagnostics and therapeutics that will result in significantly improved patient outcomes. However, current biosensing platforms with clinically relevant data streams rarely extend recording beyond short time periods. This is due to inadequate powering solutions, such as bulky electrochemical power supplies and biointerfaces that degrade rapidly requiring intervention by users or health care providers, thus limiting the utility for exploratory, screening, diagnostic and therapeutic applications.

The musculoskeletal system is an understudied area due to lack of suitable tools. However, the musculoskeletal system is an area where wireless, battery-free interfaces are critical to evolve drug discovery, diagnostic and therapeutic capabilities. Just one example of clinical need are fragility fractures associated with osteopenia and osteoporosis that account for more hospital bed days than myocardial infarction, breast cancer or prostate cancer. These fractures cause high mortality and long-term disability with health care cost over $25 billion per year by 2025.

Osteoporosis, which can be described as a silent disease, goes undetected and undiagnosed in more than 50% of cases. Due to its asymptomatic nature early on, osteoporosis is rarely detected in its earlier stages (described as osteopenia) unless patients subject themselves to preventive screening. Only until a fracture occurs will osteoporosis be diagnosed and begin to be treated. Though different tests, such as Bone Mineral Density (BMD) testing, which provides evidence of the progression of osteoporosis, through monitoring of bone calcium changes, or bone strength changes (estimated using Finite Element Modeling (FEM), can estimate the severity of osteoporosis. However, the most significant task or need in the diagnosis and treatment of osteoporosis is improving screening methods by monitoring bone deformation which is a quantitative indicator of bone strength as the disease progresses.

The present invention features device platform that uses intimate integration with the osseosurface, the surface of the bone, to enable chronic monitoring of the musculoskeletal system in small and large animal models and lays the foundation for clinical diagnostic tools that can be operated using broadly available near field communication (NFC) standard in deep tissue. The wireless, battery-free, and fully-implantable devices as described herein and named osseosurface electronics, can be attached to the surface of bones during orthopedic surgeries and form a chronic interface with bone tissues to directly record a multitude of physiological and biophysical signals critical for the assessment of musculoskeletal health and deliver stimulation in real time (FIG. 2A), providing a powerful point-of-care platform to facilitate rehabilitation and to manage musculoskeletal diseases.

BRIEF SUMMARY OF THE INVENTION

It is an objective of the present invention to provide a sensor device that combines a sensor, amplification, preprocessing and energy harvesting for battery free operation and transmission in a single small device as well as a method to anchor the device to the bone that allows for accurate sensing of bone strain i.e. deformation and reporting of the strain and loads passing through the bone for an extended period of time which ultimately allows the user to detect strain and load changes in real time each time the device is activated, as specified in the independent claims. Embodiments of the invention are given in the dependent claims. Embodiments of the present invention can be freely combined with each other if they are not mutually exclusive.

Bones as a sensor surface and stimulation location offer tremendous advantages for chronic biointerfaces because devices can be permanently bonded and provide stable optical, electromagnetic and mechanical impedance to the surface over the course of years. The presenting invention features a new class of wireless battery-free devices, named osseosurface electronics, which feature soft mechanics, an ultra-thin form factor and miniaturized multimodal biointerfaces comprised of sensors and optoelectronics directly adhered to the surface of the bone. Potential of this fully implanted device class is demonstrated via real-time recording of bone strain, millikelvin resolution thermography and delivery of optical stimulation in freely-moving small animal models as described herein. Battery-free device architecture, operation in deep tissue in large animal models and readout with a smartphone that has highlighted suitable characteristics for exploratory research and utility as a diagnostic and therapeutic platform have been demonstrated. In some embodiments, the devices described herein are implanted during an orthopedic surgery and may be used to monitor the healing process and/or used to monitor refracture, which occurs with osteoporosis.

In some aspects, the present invention features an implantable sensor device for monitoring of the musculoskeletal system. In other aspects, the present invention features an implantable sensor device for monitoring of the skeletal system. In some embodiments, the sensor device is comprised of a strain gauge which interfaces with the bone via calcium phosphate ceramic particles, operatively coupled to the analog front end. In some embodiments, the sensor device is comprised of an analog front end, which amplifies the information from the sensor gauge, operatively coupled to a processor. In some embodiments, the sensor device is comprised of a processor, which digitalizes the information from the analog front end, and is operatively coupled to a radiofrequency (RF) transmitter. In some embodiments, the sensor device is comprised of an RF transmitter, which sends the information to an external reader. In some embodiments, the sensor device is comprised of an energy harvesting system, which harvests energy from an external reader and is operatively coupled to the RF transmitter. In other embodiments, the sensor gauge measures changes in bone strain. In some embodiments, the implantable sensor device is permanently attached to the bone via a calcium ceramic particle coating. In some embodiments, the sensor device receives power from the RF transmitter. In some embodiments, the sensor device operates without a battery. In some embodiments, the devices described herein may be used for diagnosing or facilitating the treatment of osteoporosis.

The present invention may also feature a method of diagnosing or facilitating treatment of osteoporosis in a patient in need thereof. In some embodiments, the method comprises implanting a sensor device as described herein onto a surface of the patient's bone, wherein the sensor is attached to the bone surface. In some embodiments, the sensor device is attached to the bone surface via a calcium phosphate ceramic particle coating. In some embodiments, the method comprises of monitoring the patient's bone strain changes by using the strain gauge to measure the bone strain changes. In other embodiments, the bone strain changes of the patient's bone correspond to the presence or state of osteoporosis or worsening of the osteoporosis.

One of the unique and inventive technical features of the present invention is a sensor device that combines a sensor and transmitter in a single small ultra-thin device with soft mechanics that can conform seamlessly to the bone as well as a method that uses calcium phosphate ceramic particles to anchor the device to the bone. Without wishing to limit the invention to any theory or mechanism, it is believed that the technical feature of the present invention advantageously provides for a turn-key system that can be used by any patient rather than requiring a custom-made device. Additionally, the use of calcium phosphate particles to anchor the device to the bone ensures that the device reads accurately for as long as the system is functional, or the patient is alive. Furthermore, the present device is able to utilize a smartphone as the device's power supply and receiver. None of the presently known prior references or work has the unique, inventive technical feature of the present invention.

Moreover, the prior references teach away from the present invention. For example, prior devices require a long wire to connect the sensor to the transmitter, which ultimately requires the device to be customized to each patient. Further still, prior devices were attached to the bone via glue, which, ultimately, only works temporarily. Additionally, when using the glue in test animals, readings are available immediately, but the animal is often lame for a few days following surgery. Over time the glue eventually dissolves, and less accurate readings are detected.

Furthermore, the inventive technical features of the present invention contributed to a surprising result. For example, a combination of resorbable calcium phosphate ceramic particles when combined with non-resorbable calcium phosphate ceramic particles in a blend, form a bonding platform that provides more rapid secure bone bonding in comparison to unblended particles of either type. The bond, which occurs by the bone growing and chemically attaching to the device, enables a stable platform that allows for a long-lasting bond to the entire device in human and animal applications and enables superior sensor fidelity over a long period of time. Coupled with the battery free operation the platform enables exceptionally long operational times not possible with contemporary bioelectronics.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A and 1B show a systematic overview of the device of the present invention. FIG. 1A shows the exploded view schematic of the system, highlighting the constituent layers. Inset: close-up view of the bio-interface that contains the strain gauge, FIG. 1B shows a block diagram that describes the operational principles of the system.

FIGS. 2A, 28, 2C, 2D, 2E, and 2F show the osseosurface electronics: concept, device architecture, and implementation strategies. FIG. 2A shows an illustration of osseosurface electronic systems that are permanently bonded to the bone and operate wirelessly to continuously monitor biophysical signals such as bone strain, local temperature, and to deliver optical stimulation to the bone and surrounding tissues. FIG. 2B shows a photograph of an osseosurface device designed for studies in large animal models. FIG. 2C shows a layered makeup of the osseosurface system and its constituent layers. Inset features a close-up view of the multifunctional biointerface comprising a metal foil strain gauge, an NTC (negative temperature coefficient) thermistor and a μ-ILED. FIG. 2D shows a photograph of an ossesurface device attached to the surface of a sheep humerus. FIG. 2E shows a functional block diagram of osseosurface electronics comprising an external near field communication (NFC) reader that provides power and facilitates wireless communication, and an implanted system that contains active power management, operational control, analog front-end (AFE) and biointerface. FIG. 2F shows a photograph of a rat (2 weeks after surgery) implanted with an osseosurface device where the main electronics reside on the back while the biointerface is routed and attached on the left femur.

FIGS. 3A, 3B, 3C, 3D, 3E, 3F, 3G, 3H, and 3I show the system characteristics of osseosurface electronic systems. FIGS. 3A, 3B, and 3C show the device used for large animal models. FIG. 3A shows a photograph of the device. FIG. 3B shows the harvested power and voltage as functions of electrical load. FIG. 3C shows the spatial distribution of harvested power using a hand-held TX antenna at a load of 300Ω. FIGS. 3D, 3E, and 3F show the device used for small animal models. FIG. 3D shows a photograph of the device. FIG. 3E shows the harvested power and voltage as functions of electrical load. FIG. 3F shows the spatial distribution of harvested power using a 45 cm×12 cm TX antenna measured with a load of ~900Ω. FIG. 3G shows the power consumption of the device operating at different modes: I. temperature sensing; II. temperature and strain sensing; and III. temperature and strain sensing, and optical stimulation. Modes II. and III. are represented by dashed lines in FIGS. 3B and 3E that indicate the value of electrical load and power consumption. FIG. 3H shows the data rate of wireless communication for a large animal device (immersed in PBS solution) read and powered by a hand-held TX antenna as a function of antenna to device distance. The inset of FIG. 3H, shows a 3D rendering of the experimental setup. FIG. 3I shows a demonstration of long-term data recording, for a small animal device (immersed in PBS solution), measured with the 45 cm×12 cm TX antenna on a custom-built metal-free rat treadmill with back-and-forth motion at a speed of 25 cm/s. Wireless results are benchmarked against environmental temperature recorded by a thermometer (standard line) placed in close proximity. Inset, 3D rendering of the experimental setup.

FIGS. 4A, 4B, 4C, 4D, 4E, 4F, 4G, 4H, and 4I show the biointerface bench-top characterization. FIGS. 4A, 4B, and 4C show the wireless strain sensor. FIG. 4A shows a comparison of strain-load curves measured using a gold standard wired system and osseosurface electronic device in physiologically relevant range. Inset shows photograph of the bench-top test setup. FIG. 4B shows a strain profile measured with the osseosurface electronic device under progressively increasing load. FIG. 4C shows the strain profiles measured with gold standard wired system and osseosurface electronic device under sinusoidal cyclic loads. FIGS. 4D, 4E, and 4F show the optical stimulation modality. FIG. 4D shows the photographs of devices inserted at the bone-tissue interface, with μ-ILED on the bottom (left), on the top (middle) and on both sides (right). FIG. 4E shows the current profile of μ-ILED operating at frequencies of 5 Hz, 10 Hz and 20 Hz with pulse width of 20 ms. FIG. 4F shows the current and optical power as function of μ-ILED driving voltage. FIGS. 4G, 4H and 4I show the wireless thermography. FIG. 4G shows the wirelessly recorded analog to digital converter (ADC) values as function of temperature in the physiologically relevant range. FIG. 4H shows the characterization of wireless thermography capabilities using an external micro-heater to induce fast thermal variation, demonstrating a sensing resolution of <10 mK. Inset shows experimental setup. FIG. 4I shows the thermal impact of the μ-ILED operating at increasing optical powers and duty cycles in PBS solution measured wirelessly with the co-located thermistor. Inset shows experimental layout.

FIGS. 5A, 5B, 5C, 5D, 5E and 5F show the mechanical design and characterization of osseosurface electronic devices designed for rodents. FIG. 5A shows a micro-CT scan of a rat implanted with an osseosurface electronic device. FIG. 5B shows a photograph of the self-similar serpentine interconnects stretched to 250% (upper) and finite element analysis (FEA) strain profile of the serpentine interconnects stretched to 250% (lower). FIG. 5C shows the resistance of the interconnects at 0 and 250% strain during cyclic stretching to 250% for 10,000 cycles. FIG. 5D shows the FEA of the biointerface when the bone is compressed by 1000με while the serpentine interconnects are in two states: i. relaxed (0% strain); ii. stretched (250% strain). FIG. 5E shows the wirelessly recorded ADC values when the strain gauge is cyclically loaded and unloaded while the serpentine interconnect is strained to 250%, and the inset shows the test setup with 250% strain applied. FIG. 5F shows the wirelessly recorded ADC values when the strain gauge is cyclically loaded and unloaded after the serpentine interconnect has been strained for 0 cycle, 5000 cycles and 10000 cycles.

FIGS. 6A, 6B, 6C, 6D, and 6E show some in-vivo studies in rodents. FIG. 6A shows a photograph of the rat implanted with an osseosurface electronic device featuring optical stimulation capabilities with an μ-ILED attached on the left femur illuminated through the muscle and skin. FIG. 6B shows a temperature profile recorded in-vivo during recovery after implantation surgery. Inset shows 3D rendering of the home cage and TX antenna. FIG. 6C shows a strain profile recorded in-vivo using the 45 cm×12 cm TX antenna on the rat treadmill. FIGS. 6D and 6E show a deep neural network analysis of the rat's gait: before surgery, 1 week after surgery and 2 weeks after surgery. FIG. 6D shows photographs of the rat walking on the treadmill overlaid with the trace and velocity data points of the paw. FIG. 6E shows the spatiotemporal gait characteristics, including stride frequency, stride length and duty factor.

FIGS. 7A, 7B, 7C, 7D, 7E, and 7F show in-situ studies in sheep, and diagnostic application. FIG. 7A shows a photograph of a wirelessly powered osseosurface electronic device attached to a sheep humerus. FIG. 7B shows a temperature profile during implantation surgery of a sheep humerus recorded wirelessly through tissue. FIG. 7C shows a strain profile of a 3-point bending test of a sheep humerus recorded wirelessly through tissue. FIG. 7D shows tools and strategy to attach osseosurface devices on the bone: i. Bone surface is roughened by light sanding; ii. Device with applied glue is brought into contact with the bone surface with applicator; iii. Device is pressed firmly with finger; iv. Applicator is removed. FIG. 7E shows photos of demonstration of real-time signal recording through porcine skin (~1 cm thick) using an NFC-enabled smartphone: i. Device attached on the sheep humerus ii. Device covered by porcine skin and real-time signal readout with NFC-enabled smartphone. FIG. 7F shows relative data rate and power availability as functions of tissue thickness. Inset shows photograph of experimental setup FIGS. 8A, 8B, 8C, and 8D show the depictions of the technology used to secure gauge-to-bone attachment with the use of a Calcium Phosphate Ceramic (CPC) particle coating. FIG. 8A shows the sensor gauge (110) backing coated with CPC particles. FIG. 8B shows the sensor gauge (110) shown edge-on with a CPC particle coating. FIG. 8C shows a scanning electron microscope image of direct bone bonding to a CPC particle coated strain gauge (110) on a patient's vertebra. FIG. 8D shows a light microscope image of bone bonded to a strain gauge (110) backing. G is the gauge, C2 is a CPC particle; calcium phosphate ceramic particle, NB is new bone formed in order to attach to the CPC particles, CB is cortical bone, OB is an osteoblast (a bone forming cell), OC is an osteoclast (a bone digesting cell), PS is the plastic bonding substance used to bond the CPC particles to the surface of the strain gauge.

FIG. 9 shows the circuit layout including the main electronics and the biointerface, and list of components used.

FIGS. 10A, 10B, and 10C show the strategy for attaching devices described herein to the bone. FIG. 10A shows a 3D rendering of the applicator with dimensions suitable for the sheep humerus and devices with a footprint of 2.5 cm×1.5 cm. FIG. 10B shows a step-by-step procedure of attaching a small footprint (1.5 cm×1 cm) device on the sheep humerus. FIG. 10C shows a step-by-step procedure of attaching a device (2.5 cm×1.5 cm) on the human femur model.

FIG. 11 shows step-by-step images of the procedures to implant the osseosurface device in rats. 1. Rat under anesthesia with fur shaved on the back and hind limb; 2. Incision made into the skin on the back and the limb; 3. Device inserted subcutaneously on the back; 4. Bio-interface being tunneled subcutaneously to the hind limb; 5. Closing the skin on the back by suturing; 6. Femur exposed; 7. Attaching the biointerface on the femur; 8. Biointerface attached; 9. Incision on the limb closed by suturing.

FIG. 12 shows a photograph of the setup for measuring the power harvesting capability and wireless data communication performance through thick tissues.

FIG. 13 shows the stability of serpentine interconnects. Wirelessly recorded ADC reading from the strain sensor (gain~215, strain gauge unloaded) while the serpentine interconnects are cyclically stretched from 2 cm to 7 cm. Insets, photographs of the serpentine interconnects being stretched to different length: i. relaxed (2 cm); ii. 4 cm; iii. 7 cm.

FIGS. 14A, 14B, 14C, 14D, 14E, and 14F show a circuit simulation of the analog front end of strain sensor (FIG. 14A-14D) and thermography (FIG. 14E-14F). FIGS. 14A and 14B show output voltages from the Wheatstone bridge and the instrumentation amplifier as the resistance of the strain gauge varies from 999Ω to 1001Ω (corresponding to strain from −500με to 500με) following a sinusoidal waveform (20 Hz): circuit diagram with simulation conditions (FIG. 14A) and simulation results (FIG. 14B). FIGS. 14C and 14D show output voltage from the Wheatstone bridge as the bridge resistors, R1 and R2, vary from 1 kΩ to 10 kΩ for strain of 500με and 1000με: circuit diagram with simulation conditions (FIG. 14C) and simulation results (FIG. 14D). FIGS. 14E and 14F show output voltages from the Wheatstone bridge and the instrumentation amplifier as the temperature varies from 32° C. to 42° C.: circuit diagram with simulation conditions (FIG. 14E) and simulation results (FIG. 14F).

FIGS. 15A, 15B, 15C, and 15D show the thermal stability of the strain sensor analog front-end. FIG. 15A shows resistance of the 350Ω gauge and 1000Ω gauge as functions of temperature. FIG. 15B shows the output voltage from the Wheatstone bridge as a function of temperature. Inset, circuit diagram. FIG. 15C shows the output voltage from the instrumentation amplifier as a function of temperature. FIG. 15D shows the wirelessly recorded ADC reading as a function of temperature.

FIGS. 16A, 16B, and 16C show a comparison of the power harvesting capability of devices with and without NFC SoC. FIG. 16A shows a 3D rendering of the RX antenna with a Cu trace width of 120 μm and inter-trace distance of 60 μm. FIG. 16B shows the power harvesting capability, i.e. rectified voltage and harvested power as functions of electrical load, of the device without NFC SoC. FIG. 16C shows the power harvesting capability of the device with NFC SoC, showing the voltage clamping by the NFC SoC.

FIGS. 17A, 17B, 17C, 17D, 17E, 17F, 17G, and 17H show the optimization of the RX antenna. 3D rendering of RX antennas with various geometries (FIG. 17A, 17C, 17E, 17G) and the corresponding power harvesting capabilities with NFC SoC (FIG. 17B, 17D, 17F, 17H).

FIGS. 18A, 18B, 18C, 18D, 18E, and 18F show the power harvesting performance of the RX antennas in various test arenas. FIG. 18A shows the spatial distribution the harvested power with the large animal device at a load of 900Ω from a handheld TX antenna (20 cm). FIGS. 18B and 18C show the power harvesting capability (FIG. 18B) and spatial distribution of harvested power (FIG. 18C) of the small animal device with a 2-turn 33 cm×26 cm TX antenna that encloses the rat home cage. FIG. 18D-18F shows the normalized power harvesting capability as functions of rotation angle (FIG. 18D), bending radius (FIG. 18E) and 3D bending radius (FIG. 18F) of the device.

FIGS. 19A and 19B show the wireless communication performance. FIG. 19A shows the data rate of the rat device in various locations in the treadmill cage (2-turn, 45 cm×12 cm). FIG. 19B shows the data rate of the rat device in various locations in the home cage (2-turn, 33 cm×26 cm).

FIGS. 20A and 20B show the bench top tests of the wireless strain sensor attached on a sheep femur specimen. Load, strain recorded by the wired sensor and wireless device when the femur is subjected to cyclic loads with square (FIG. 20A) and triangle (FIG. 20B) waveforms.

FIGS. 21A, 21B, 21C and 21D show the bench top characterization of the wireless thermography. FIG. 21A shows the design layout of the micro-heater. FIG. 21B shows the thermal impact of the μ-ILED in PBS as a function of operation frequency (duty cycle ~50%, optical power ~100 mW/mm2) recorded wirelessly by the co-located NTC thermistor. FIG. 21C shows the thermal impact of an LED as functions of driving current and duty cycle (frequency ~20 Hz) in air measured wirelessly by the co-located NTC thermistor. FIG. 21D shows the temporal profile of the thermal impact of an LED powered by the rectified voltage and controlled by a microcontroller with a duty cycle of 75% in PBS.

FIGS. 22A and 22B show FEA models and simulation conditions for the mechanical simulation. FIG. 22A shows a simulation of the strain in the Cu traces while the serpentine interconnects are stretched. FIG. 22B shows a simulation of the mechanical isolation of the strain gauge provided by the serpentine interconnects.

FIG. 23 shows the weight of the subject as a function of time post-surgery.

FIG. 24 shows the histology results of the tissues surrounding the implanted device. Microscopic graphs of the histology analysis with different amplifications, from left to right, 20×, 40× and 100×.

Figures 25A, 25B, 25C, 25D:
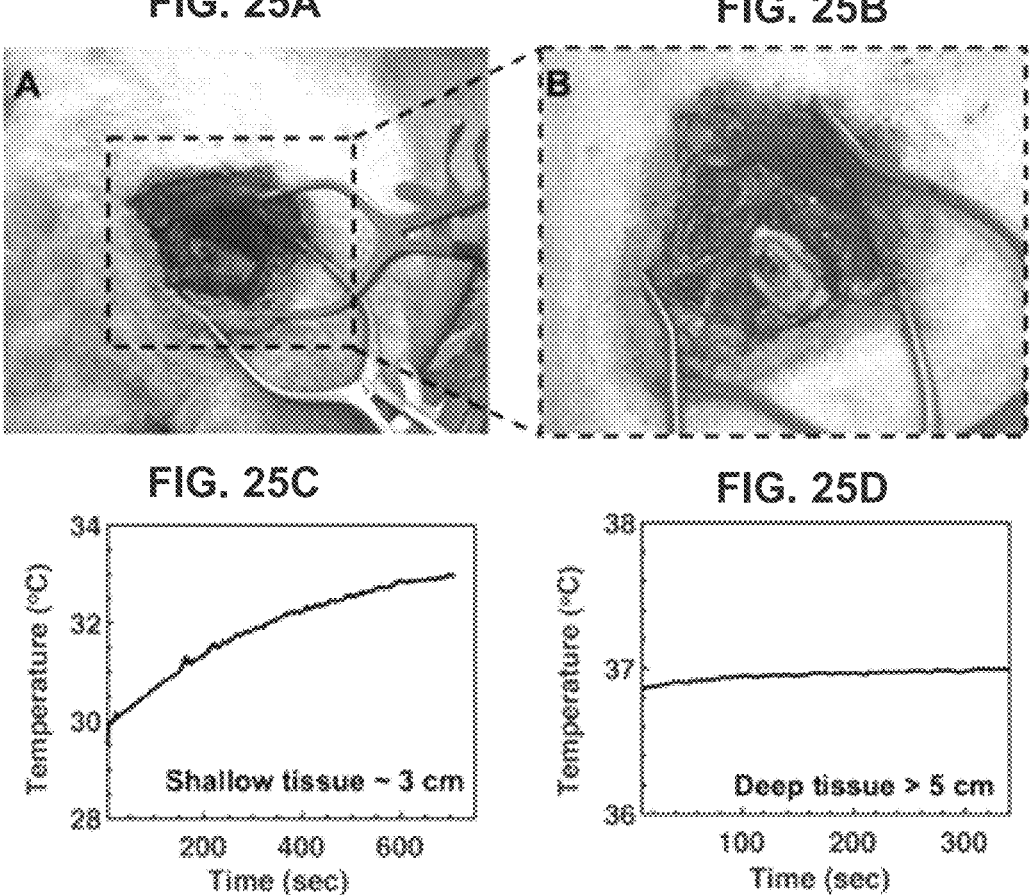

FIGS. 25A, 25B, 25C, and 25D show the in-situ study in sheep cadaver. FIG. 25A-25B shows a photograph of the sheep's left shoulder with an osseosurface electronic device attached on the surface of the humerus. FIG. 25C-25D shows the temperature profiles wirelessly recorded from different depths in the sheep cadaver: ~3 cm (FIG. 25A) and >5 cm (FIG. 25B).

DETAILED DESCRIPTION OF THE INVENTION

Following is a list of elements corresponding to each particular element referred to herein:

100 Sensor device
    110 Strain gauge
    120 Analog-front end
    130 Processor
    140 Radiofrequency (RF) transmitter
    150 External reader
    160 Energy-harvesting system Utilizing laser ablation flexible circuits structuring technology, or any other flexible circuit definition technology, a strain sensing device and battery-free radio transmitters can be produced and coated with a blend of calcium phosphate ceramic (CPC) particles to create an inexpensive miniature device capable of sensing bone strain and when calibrated appropriately, reporting both bone strains and loads passing through bone for extended periods of time once bone attachment to the CPC coated device is complete. The highly miniaturized and flexible system can be integrated with the coating that will encourage rapid direct attachment of the device to the bone, which will ensure direct accurate measurement and transmission of strains and subsequently loads passing through the bone at the location where the sensor is activated. The present invention also features a process for preparing the calcium ceramic particle coating, a process for preparing the monolithic sensor and transmitter, receiver, and energy harvester circuit integration, and a process for coating the device with calcium phosphate ceramic particles in order to ensure exposure of the particles to a bone surface so that rapid bone bonding can occur. In addition, the software and external radio frequency hardware used to readout the sensor is an embodiment of the present invention.

Referring now to FIGS. 1A-25D, the present invention features an implantable sensor device. In some embodiments, the implantable sensor device may be used for the diagnosis and facilitation of treatment for osteoporosis. In other embodiments, the implantable sensor device may be used in other applications not limited to osteoporosis.

In one embodiment, the present invention features an implantable sensor device (100) for monitoring of the musculoskeletal system. In another embodiment, the present invention features an implantable sensor device (100) for monitoring of the skeletal system. In a further embodiment, the present invention features an implantable sensor device (100) for measuring bone deformation (i.e., bone strain). In some embodiments, the sensor device (100) comprises a strain gauge (110) which interfaces with the bone via calcium phosphate ceramic (CPC) particles and is operatively coupled to the analog front end (120). In some embodiments, the sensor device (100) comprises an analog front end (120), which amplifies the information from the sensor gauge (110), and is operatively coupled to a processor (130). In some embodiments, the sensor device (100) comprises a processor (130), which digitalizes the information from the analog front end (120), and is operatively coupled to a radiofrequency (RF) transmitter (140). In some embodiments, the sensor device (100) comprises an RF transmitter (140), which sends the information to an external reader (150). In some embodiments, the sensor device (100) comprises an energy harvesting system (160), which harvests energy from an external reader (150) and is operatively coupled to the RF transmitter. In other embodiments, the sensor gauge (110) measures changes in bone strain. In some embodiments, the implantable sensor device (100) is permanently attached to the bone via a calcium ceramic (CPC) particle coating. In some embodiments, the implantable sensor device (100) is semi-permanently attached to the bone via a cyanoacrylate adhesive. In some embodiments, the devices described herein may be used for diagnosing or facilitating the treatment of osteoporosis.

In some embodiments, the devices described herein are attached via an instant adhesive. As used herein an instant adhesive is a one-component, solvent-free, fast-setting cyanoacrylate adhesive. In other embodiments, the devices described herein are attached via a cyanoacrylate adhesive. In some embodiments, cyanoacrylates polymerize within seconds in the presence of a weak base, such as surface moisture, and will bond well to a wide range of substrates. In some embodiments, the cyanoacrylate adhesive allows for the immediate bonding of the device to the bone surface. Without wishing to limit the present invention to any theory or mechanism it is believed that the cyanoacrylate adhesive allows for quick bonding which is essential for immediate measurements and to facilitate getting through surgical placement quickly. In some embodiments, other forms of instant adhesive may be used. In other embodiments, other forms of adhesive may be used. In further embodiments, the present invention is not limited to using instant adhesive, and may also use any other appropriate adhesives that set within the time frame of the surgery being performed to insert the device.

In some embodiments, the cyanoacrylate adhesive degrades over a period of up to 2 weeks. In some embodiments, the cyanoacrylate adhesive degrades over a period of up to 3 weeks. In some embodiments, the cyanoacrylate adhesive degrades over a period of up to 4 weeks. In some embodiments, the cyanoacrylate adhesive degrades over a period of up to 5 weeks. In some embodiments, the cyanoacrylate adhesive degrades over a period of up to 6 weeks. In some embodiments, blood at the attachment site (i.e., the bone surface) of the device (100) can decrease the period of time in which the cyanoacrylate adhesive degrades. Therefore, in some embodiments, the period of time at which the cyanoacrylate adhesive degrades depends on how vascular the attachment site of the device (100) is. In other embodiments, the period of time at which the cyanoacrylate adhesive degrades depends on how much blood there is at the attachment site of the device (100) after the patient's surgery is complete.

In other embodiments, the devices described herein are attached via a calcium ceramic (CPC) particle coating. In some embodiments, the devices described herein are attached to the bone via a calcium ceramic (CPC) particle coating. In some embodiments, once bonded to the bone the CPC particle coating is permanent. In other embodiments, the CPC particle coating provides for an interface between the device and the bone that is permanent.

In some embodiments, the CPC particle coating takes up to 1 week to bond to the bone. In some embodiments, the CPC particle coating takes up to 2 weeks to bond to the bone. In some embodiments, the CPC particle coating takes up to 3 weeks to bond to the bone. In some embodiments, the CPC particle coating takes up to 4 weeks to bond to the bone. In some embodiments, a dissolving suture may be placed over the device to hold the device in place while bonding occurs. In some embodiments, the rate at which the CPC particle coating bonds to the bone depends on how vasculate the attachment site of the device is. In some embodiments, a highly vascular attachment site will allow for faster bonding of the CPC particle coating to the bone. In other embodiments, the rate at which the CPC particle coating bonds to the bone may depend on the age of the patient. For example, in a younger patient which grows bone more quickly allows for fast bonding of the CPC particle coating to the bone.

In further embodiments, devices described herein are attached to the bone with an instant adhesive and a calcium ceramic (CPC) particle coating. In some embodiments, devices described herein are attached to the bone with a cyanoacrylate adhesive and a calcium ceramic (CPC) particle coating. In some embodiments, the instant adhesive (i.e., cyanoacrylate adhesives) is placed around the perimeter of the device. In other embodiments, the instant adhesive (i.e., cyanoacrylate adhesives) is placed around the perimeter of the CPC particle coated device. Without wishing to limit the present invention to any theories or mechanisms it is believed that the use of both a cyanoacrylate adhesive and a calcium ceramic (CPC) particle coating allows the devices described herein to bond instantly with the cyanoacrylate but over time as the cyanoacrylate is dissolved by the body the calcium coated section of the device will be permanently bonded by bone.

In some embodiments, the sensor device (100) may be attached to a bone as a single platform (i.e., the sensor gauge (110) or biointerface and the rest of the device (e.g., the analog front end (120), the processor (130), the radiofrequency (RF) transmitter (140) and the energy harvesting system (160)) are all on one platform). Without wishing to limit the present invention to any theory or mechanisms it is believed that a sensor device (100) as a single platform allows for an easier installation of the sensor device (100) during surgery. In other embodiments, the sensor device (100) may be installed in separate pieces. For example, the sensor gauge (110) or biointerface may in integrated onto a long bone of the subject/animal and the rest of the device (i.e., the analog front end (120), the processor (130), the radiofrequency (RF) transmitter (140) and the energy harvesting system (160)) is placed under the skin along the back (see FIG. 2F and FIG. 11). In some embodiments, the sensor gauge (110) and the rest of the device are attached via thin wires. Without wishing to limit the present invention to any theory or mechanisms it is believed that the decision to install a device as described herein as a single platform or as separate pieces depends on the size of the subject/animal and the size of the bone in which the device is to be placed and the presence of additional materials or implants.

Figure 1A:
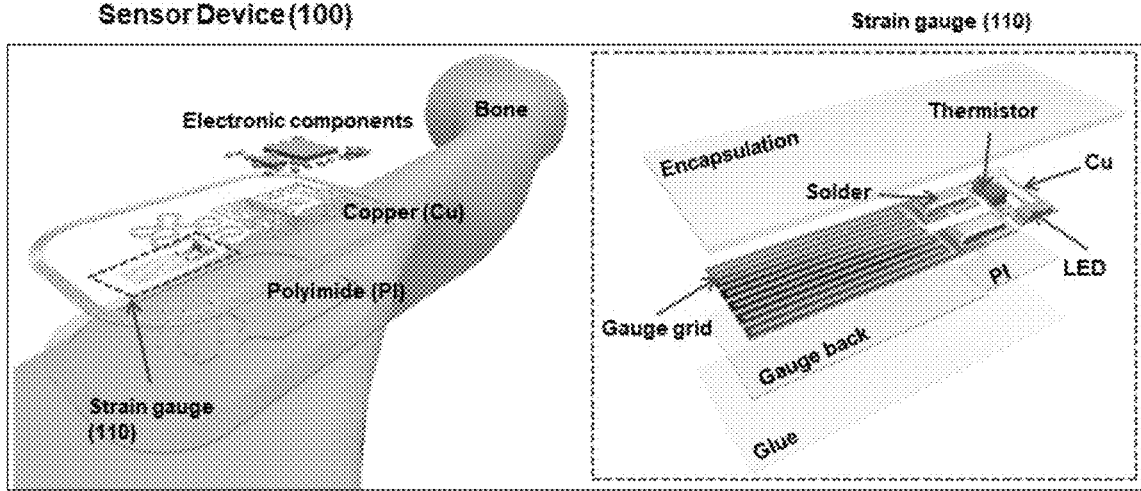
Figure 1B:
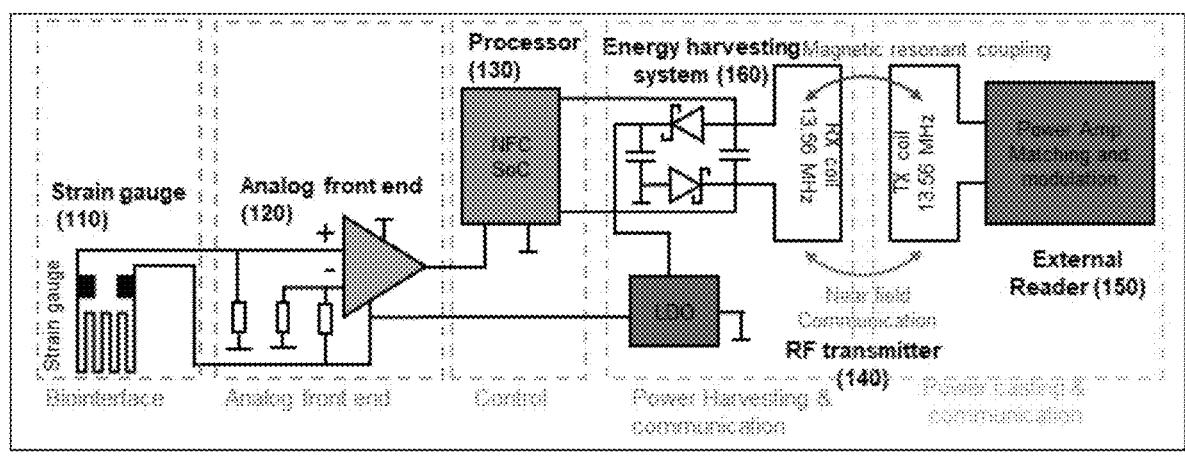

FIG. 1A and FIG. 1B shows schematic views of the components of the implantable sensor devices (100) of the present invention. The present invention is not limited to the materials and configurations shown herein.

In some embodiments, the sensor devices (100) described herein are further comprised of a thermistor operatively coupled to the analog front end (120). As used herein, a "thermistor" refers to a temperature sensor, in particular a thermistor exhibits a large change in resistance proportional to a change in temperature. In some embodiments, the thermistor is a negative temperature coefficient (NTC) thermistor. In other embodiments, the thermistor is a resistive thermistor. In further embodiments, the devices described herein may utilize other temperature sensors and/or temperature sensing techniques such as thermocouples. In some embodiments, the sensor devices (100) described herein further comprises a light emitting diode (LED) operatively coupled to the processor (130). In some embodiments, the LED is a microscale inorganic light-emitting diode (μ-ILED). In other embodiments, the LED is an organic LED (OLED). In further embodiments, the light-emitting diode (LED) is any LED that is small enough to fit within the sensor devices (100) described herein.

In some embodiments, a biointerface of the device comprises a strain gauge (110), a thermistor and an LED. In some embodiments, the biointerface of the devices described herein enables simultaneous recording of local biophysical signals and on-demand delivery of exogenous stimulation. In some embodiments, the local biophysical signals comprise bone strain and/or local temperature. In some embodiments, the exogenous stimulation is provided by an optical stimulation to the bone and surrounding tissues.

In some embodiments, the devices (100) described herein are used for monitoring of the musculoskeletal system. In other embodiments, the devices (100) described herein are used for monitoring of the skeletal system. In some embodiments, monitoring of the musculoskeletal system may comprise diagnosing and/or facilitating the treatment of osteoporosis. Non-limiting examples of potential applications of the device (100) include but are not limited to monitoring nonunion fractures, arthrodesis sites, stress fractures, and monitoring the rehabilitation of bone and soft tissue procedures.

Without wishing to limit the present invention to any theories or mechanisms it is believed that bone stiffness and strength are interrelated due to the composition (i.e., how much calcium there is in the bone) and structure of the bone. Therefore, the devices (100) described herein monitor the stiffness of bone which can help indicate the strength of the bone, and thus its potential to fracture.

In some embodiments, the devices (100) described herein would take absolute measurements. In other embodiments, the devices (100) described herein would take chronic measurements. Without wishing to limit the present invention to any theories or mechanisms it is believed that chronic measurements will establish a baseline peak strain and/or strain pattern for a patient during normal activities. Acute changes to the peak strains and/or strain patterns from a patient's baseline could indicate an underlying structural issue and potentially pending fracture. In further embodiments, the devices (100) described herein, may determine a subject's risk of fracture by using the strain measurements to monitor parameters specific to the patient's gait. For example, a subject with an unsteady or uncoordinated gait pattern may be more prone to falls and therefore more prone to fractures.

As used herein, "osteoporosis" refers to a bone disease that occurs when the body loses too much bone, makes too little bone, or both, which result in bones becoming weak. Osteoporosis is a continuum of bone mineral density currently characterized by a T-score (which looks at bone mineral density (BMD)), however, the T-score does not relate to the risk of fracture in a patient because bone structure also affects bone stiffness and strength. In some embodiments, the sensor devices described herein may be used to determine the risk of fracture in a patient. In some embodiments, the sensor devices described herein measures the changes in bone stiffness which are directly related to the risk of fracture in a patient.

In some embodiments, the implantable sensor device (100) can be utilized with other components for treatment of osteoporosis. In some embodiments, the sensor device (100) can be utilized with other devices. In some embodiments, those devices may include but are not limited to an implanted device that allows the release of chemicals or molecules that are known to induce new bone formation. In some embodiments, examples of chemicals or molecules known to induce new bone formation may include, but are not limited to, proteins such as TGF-beta 1, or BMP-2 or BMP-7 or any combination of these.

In some embodiments, the bone strain measured by the strain gauge (110) is amplified by the analog front end (120) and converted to digital signals by the processor (130), and the electronic signals are transmitted by the RF transmitter (140) to the receiver. In some embodiments, the external reader (150) is external to a body in which the sensor device (100) is implanted.

In some embodiments, the implantable sensor device (100) is capable of sensing bone strain, and when calibrated appropriately, reports loads passing through the bone for extended periods of time once bone attachment to the sensor device (100) is completed.

As used herein, an "extended period of time" may refer to a period that ranges from a week to years. As a non-limiting example, the period of time may range from 2-8 weeks, or 1-4 years, or 5-10 years, or 10-20 years. In some embodiments, an extended period of time may refer to a period of time longer than 20 years.

As used herein, "bone strain" may refer to a directional shape change divided by its original directional shape e.g. a length change directly adjacent to the location where the gauge is attached to the bone, relative to the original length of the bone-attached sensor before the strain occurred. As used herein, "load" may refer to the amount of force passing through the bone directly attached to the sensor. In some embodiments, the sensor device (100) is calibrated by using documented bone stiffness values with the strain measured in a specific location to determine the load passing through that same area of bone.

In some embodiment, the implantable sensor device (100) further comprises a near field communication system on a chip (NFC SoC). In some embodiments the NFC SoC comprises a microprocessor.

In some embodiments, the implantable sensor device (100) is further comprised of a low drop-out regulator (LDO). In some embodiments, the LDO is a DC linear voltage regulator that can regulate the output voltage even when the supply voltage is very close to the output voltage.

In some embodiments, the implantable sensor device (100) has a digital RF front end. In some embodiments, the implantable sensor device (100) uses a battery-free single-channel radio transmitter. In some embodiments, the external reader (150) is external to the body in which the sensor device (100) is implanted. In some embodiments, the external reader (150) is a smart device. In some embodiments, the external reader (150) is a smartphone. In some embodiments, a smartphone can be used to power the implantable sensor device (100). In some embodiments, the sensor device (100) is powered by a battery. In some embodiments, the sensor device (100) is wirelessly powered. In some embodiments, the power source is charged wirelessly. The present invention is not limited to the aforementioned electronics or power systems.

In some embodiments, the sensor device (100) is able to receive commands from the external reader (150). The commands can for example adjust operational parameters such as sampling rate, duty cycles, and preprocessing.

In some embodiments, the implantable sensor device (100) comprises a power source operatively coupled to the RF transmitter (140) and sensor gauge (110). In some embodiments, the implantable sensor device (100) comprises an energy harvesting system (160). In some embodiments, the energy harvesting system (160) harvest energy from an external reader (150).

In some embodiments, the strain sensing device (100) may be coated with a blend of calcium phosphate ceramic particles to facilitate attachment of the sensor device (100) to the bone. In some embodiments, the device (100) may be attached to long bones, short bones, flat bones, or irregular bones.

In some embodiments, the sensor device (100) is integrated with a long bone. Non-limiting examples of long bones include but are not limited to a femur bone or a humerus bone. In some embodiments, the sensor device (100) can be integrated with any long bone, such as bones in the legs (e.g., the tibia, the fibula, or the femur) and/or the arms (e.g., the radius, the ulna or the humerus). In other embodiments, the sensor device (100) may be integrated with smaller bones such as fingers or toes (i.e., metacarpals or phalanges). In further embodiments, the sensor device can be integrated with smaller bones and used in combination with a muscle stimulator for example in a paraplegic patient. For example, the devices described herein could modulate grip when used in combination with a muscle stimulator in the upper arm and/or hand.

In some embodiments, devices described herein are permanently attached to the bone. In other embodiments, devices described herein are semi-permanently attached to the bone. In some embodiments, the devices (100) described herein become detached from the bone naturally (i.e., the adhesive (e.g., cyanoacrylate) is removed and/or degraded by the body). In other embodiments, the devices (100) described herein are detached from the bone via a surgeon during a surgery. In some embodiments, the devices (100) described herein are semi-permanently attached to the bone for 1 week. In some embodiments, the devices (100)

described herein are semi-permanently attached to the bone for 2 weeks. In some embodiments, the devices (100) described herein are semi-permanently attached to the bone for 3 weeks. In some embodiments, the devices (100) described herein are semi-permanently attached to the bone for 4 weeks.

Without wishing to limit the present invention to any theories or mechanisms it is believed that the CPC-particle to bone bond is a living bond, and as the bone grows it attaches chemically to the CPC particle surfaces and will remain attached for the life of the patient.

Without wishing to limit the present invention to any theories or mechanisms it is believed that one interface of the device (i.e., the cyanoacrylate attachment to the bone) gradually degrades.

In some embodiments, the devices described herein can harvest power through tissue that is about 1-10 cm thick. In some embodiments, the devices described herein can harvest power through tissue that is about 1 cm thick or about 2 cm thick or about 3 cm thick or about 4 cm thick or about 5 cm thick or about 6 cm thick, or about 7 cm thick, or about 8 cm thick, or about 9 cm thick, or about 10 cm thick. In other embodiments, the devices described herein can harvest power through tissue that is more than 10 cm thick.

Without wishing to limit the present invention to any particular theories or mechanisms it is believed that the near-field magnetic resonant coupling (13.56 MHz, specific absorption rate (SAR) <20 mW/kg12) between an external primary loop antenna (TX antenna) and the on-board loop antenna (RX antenna) enables reliable power harvesting through thick tissues with hardware that is compatible with NFC protocols widely available in portable devices.

The present invention may feature a method of preparing a calcium phosphate ceramic (CPC) particle coating. The method comprises creating a blend of calcium phosphate particles. In some embodiments, the method comprises applying a thin layer of implant grade epoxy on the gauge to bond the particles to the sensor surface (i.e., the strain gauge (110)) to which the CPC particles will be attached. In other embodiments, the method comprises applying a thin layer of implant grade epoxy on the gauge to bond the particles to the surface of the biointerface to which the CPC particles will be attached. In further embodiments, the method comprises applying a thin layer of implant grade epoxy on the gauge to bond the particles to the sensor device (100) surface to which the CPC particles will be attached. The present invention is not limited to the use of implant grade epoxy to bind the CPC particles to the sensor device (100) as described herein, and other appropriate materials may be used (e.g., polysulfone).

In some embodiments, the sensor device (100) comprises a polyimide sheet which covers the whole back side of the device. In other embodiments, other flexible substrates may be used to cover the back of the sensor device (100) which may include but is not limited to parylene. In further embodiments, the sensor device (100) may comprise a polymer carrier. As used herein, "a polymer carrier" (e.g. polyimide) may refer to a polymeric film that serves as the surface for the calcium particles to attach and also serves as the sensor and radio transmitter circuitry platform.

A polyimide sheet can be the backing material of a strain gauge. Implant-grade epoxy (IGE) (Master Bond EP42HT, Master Bond, Inc., Hackensack, NJ) was prepared according to the manufacturer's instructions. Batches of IGE weighing 0.7 grams were mixed for each group of gauges. Calcium-phosphate-ceramic (CPC) particles were blended before they were attached to the matte side of the polyimide backings of the strain gauges. A relatively amorphous tricalcium phosphate previously designated CPC 6, and a microcrystalline hydroxyapatite, previously designated CPC 7, were mixed in a 15-85% ratio by weight to make a CPC blend. A thin layer of IGE was applied to the matte side of the strain gauges. The epoxy layer was covered with the blended CPCs and gently pressed down with a silicon rubber sheet so that particles become partially embedded in the epoxy. White CPC particles visible on the surface indicated that CPC particles were attached to the epoxy but not completely embedded. Clear particles visible on the surface indicated that the particles were completely covered with IGE and therefore embedded too deeply. In some embodiments, a mixture of CPC 6, CPC 7, CPC 2, or a combination thereof may be used. In other embodiments, the CPC 2 is used independently. In further embodiments, CPC 6 and CPC 7 are combined together to form a mixture.

In some embodiments, the calcium phosphate ceramic (CPC) particles are created by blending calcium particles together. Non-limiting examples for calcium particles may include but are not limited to tricalcium phosphate and hydroxyapatite particles of various shapes.

In some embodiments, the calcium phosphate ceramic (CPC) particle blend is created by mixing tricalcium phosphate and hydroxyapatite in a 5-95% ratio by weight. In some embodiments, the CPC particle blend is created by mixing tricalcium phosphate and hydroxyapatite in a 10-90% ratio by weight. In some embodiments, the CPC particle blend is created by mixing tricalcium phosphate and hydroxyapatite in a 15-85% ratio by weight. In some embodiments, the CPC particle blend is created by mixing tricalcium phosphate and hydroxyapatite in a 20-80% ratio by weight. In some embodiments, the CPC particle blend is created by mixing tricalcium phosphate and hydroxyapatite in a 25-75% ratio by weight. The ratio may be adjusted for patients or subjects of different sexes, different ages and/or different species.

In some embodiments, the present invention may also feature a method of diagnosis or facilitating the treatment of osteoporosis in patients in need thereof. In some embodiments, the method comprises implanting a sensor device (100) as described herein onto a surface of the patient's bone. In some embodiments, the sensor device (100) is attached to the bone surface using a calcium phosphate ceramic particle coating. In some embodiments, the sensor device (100) monitors the patient's bone strain changes by using the strain gauge (110) to measure the bone strain changes. In some embodiments, the bone strain and load changes of the patient's bone correspond to the presence or change in the degree of the state of osteoporosis. In some embodiments, the patient is diagnosed with increasing osteoporosis when significant strain changes during controlled activities are detected that bring strain levels near or above bone failure strains. In other embodiments, treatment for osteoporosis may include using strain increases to activate implanted devices that release chemicals or molecules that are known to induce rapid new bone formation.

In other embodiments, the present invention features a method of determining the risk of bone fracture in a patient in need thereof. In some embodiments, the method comprises implanting a sensor device (100) as described herein onto a surface of the patient's bone. In some embodiments, the implantable sensor device (100) is attached to a bone surface via a calcium ceramic particle coating. In some embodiments, the strain gauge (110) interfaces with the bone surface and measures changes in bone strain. In some embodiments, the method comprises establishing a baseline peak strain and strain pattern for the patient using the strain gauge (110). In other embodiments, the method comprises monitoring the patient's bone strain changes by using the strain gauge (110) to measure the bone strain changes. In some embodiments, acute changes to the patients baseline peak strain and strain pattern indicate an underlying structural issue and an increased risk of bone fracture.

As used herein, bone failure strain may refer to the strain at which bone is permanently deformed and/or breaks.

Strain values during physiological loading of the trabecular bone of osteoporotic patients have not been measured. However in some embodiments, failure strength of trabecular bone was noted to be approximately 100±20 MPa., in normal individuals, while osteoporotic patients' bone strengths were on average 60% weaker. In addition, there is a significant difference between the failure strength of the bones of men and women. For example, women's bones can be about 33% weaker than men's bones.

In some embodiments, increasing osteoporosis may refer to increasing strain values which imply the bone stiffness is decreasing because bone is being lost.

In some embodiments, the sensor device (100) can measure the patient's bone load changes once properly calibrated.

In some embodiments, an external reader (150) is external to the body in which the sensor device (100) is implanted. In some embodiments, the external reader (150) may be a smart device.

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

EXAMPLE

The following is a non-limiting example of the present invention. It is to be understood that said example is not intended to limit the present invention in any way. Equivalents or substitutes are within the scope of the present invention.

Methods: Device Fabrication: Flexible circuitries were fabricated by ultraviolet (UV; 355 nm) laser ablation (ProtoLaser U4, LKPF, Germany) using a sheet of copper clad polyimide foil (Dupont, Pyralux AP8535R, Cu/Polyimide/Cu, 17.5 μm/75 μm/17.5 μm) as substrate. Subsequent sonication in solder flux and isopropanol (IPA) removed the surface oxides formed during laser ablation. Surface-mount components, including passive components such as resistors (0201, 0.6 mm×0.3 mm), capacitors, Schottky diodes (Skyworks Inc.), Zener diodes (Comchip Technology Corp., 5.6 V), μ-ILED (red, ES-AEHRAX10, EPISTAR) and NTC thermistor (NTCG064EF104FTBX, TDK), as well as active components such as metal-oxide-semiconductor field-effect transistor (MOSFET) (PMZ130UNE, Nexperia), low-dropout linear regulators (LDO, TCR2DG18, Toshiba), instrumentation amplifier (INA, AD8235, Analog Devices) and a near field communication system on a chip (NFC SoC) (RF430FRL152H, Texas Instruments), were manually placed on the flexible circuit and reflowed with low temperature solder (Indium Corp.). A metal foil strain gauge (N2A-06-S5182N-10C/E4, Micro-Measurements) was then integrated by using a chisel tipped soldering iron. Finally, the device was baked at 120° C. in an oven for 30 min to remove residual flux and solvents used during the assembling process. Device encapsulation was accomplished with a layer of Parylene C by chemical vapor deposition and polydimethylsiloxane (PDMS) (Sylgard 184, Dow Corning) by dip coating.

Figure 9:
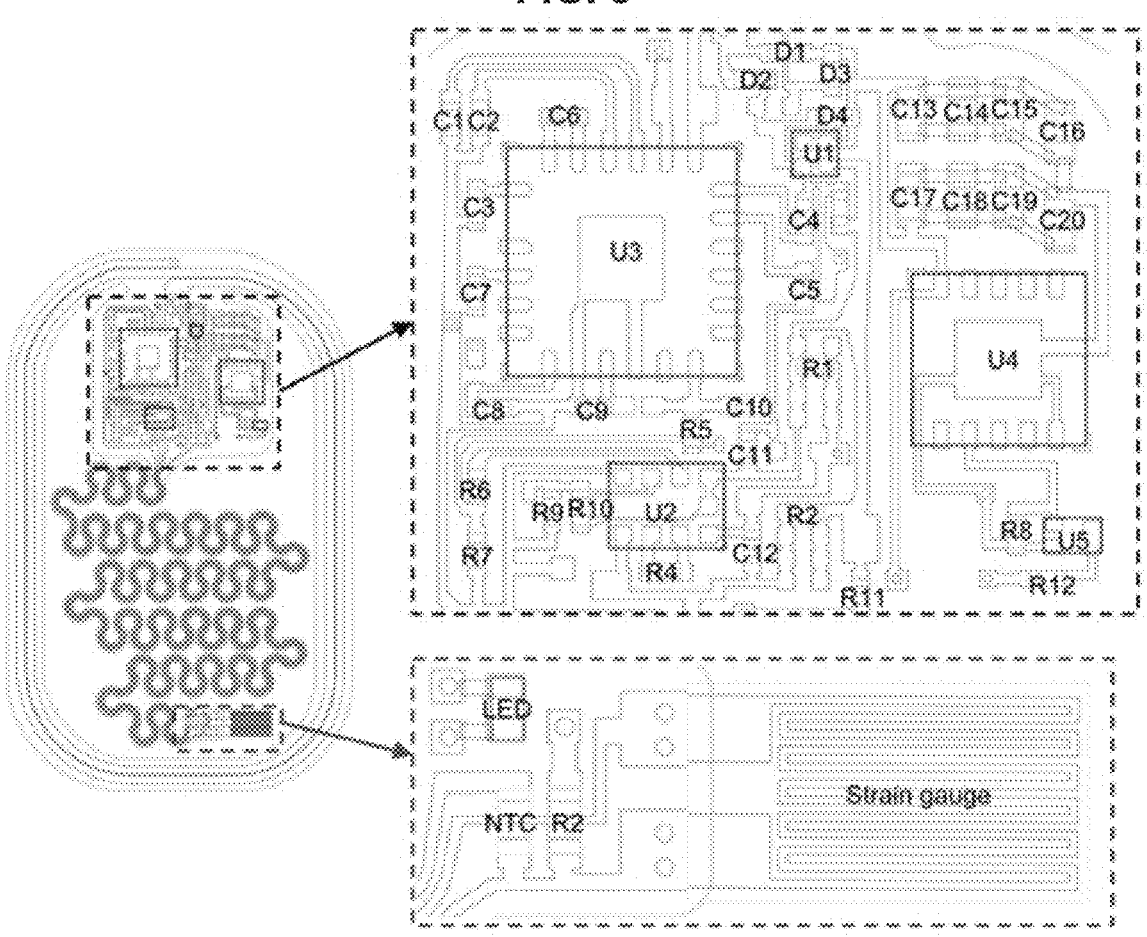
Figures 10A, 10B, 10C, 11, 12, 13:
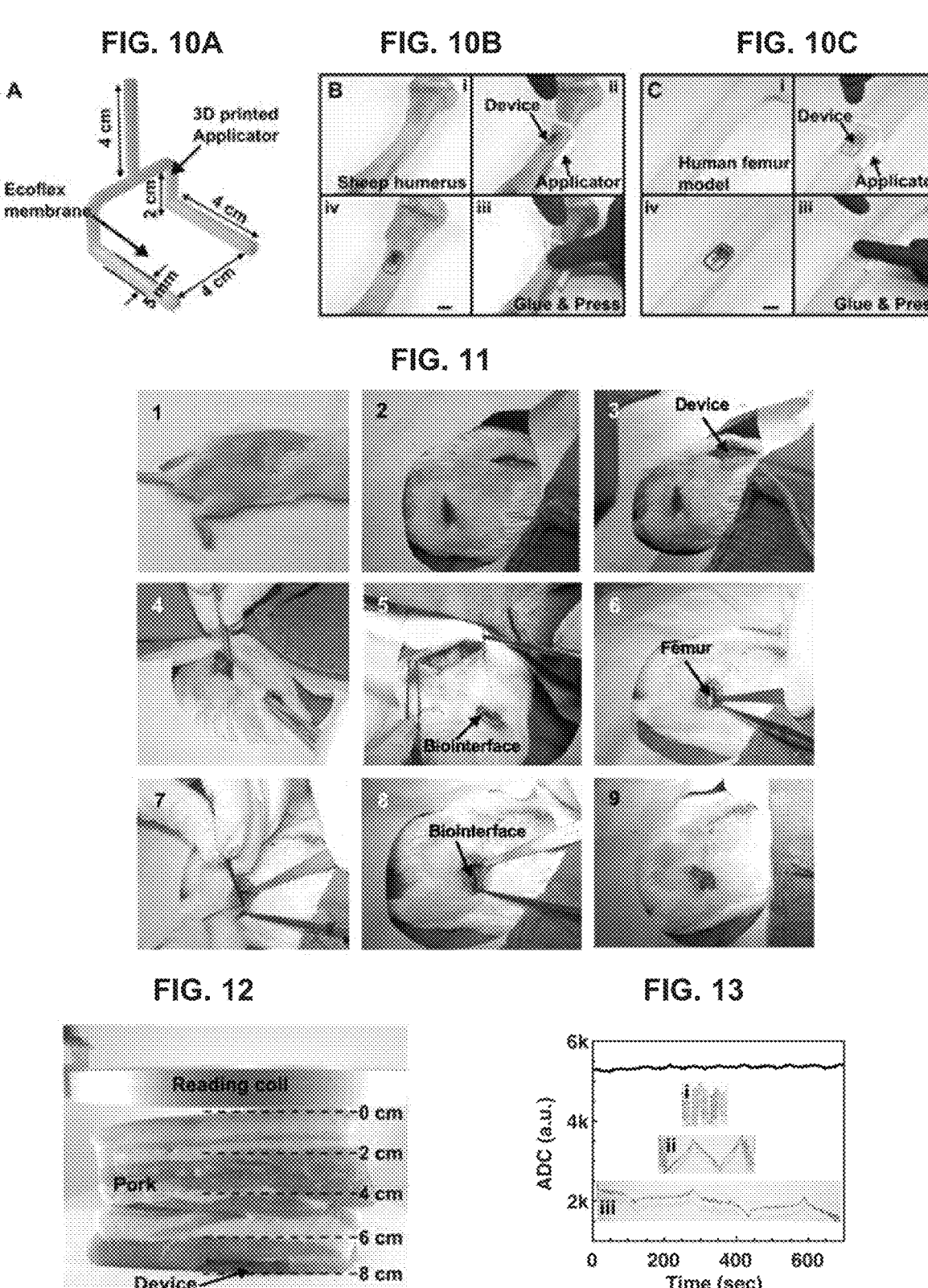
Figure 14A:
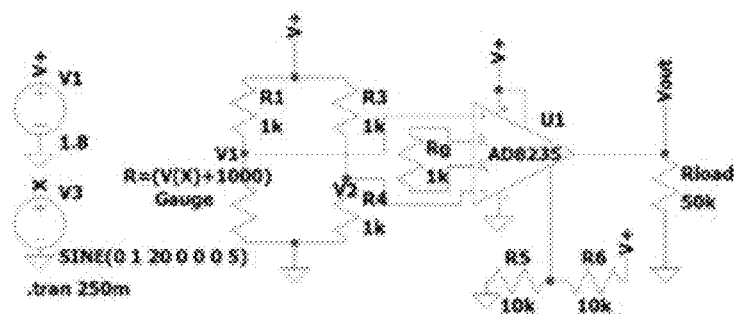
Figure 14B:
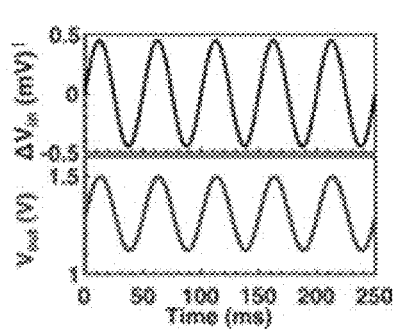
Figure 14C:
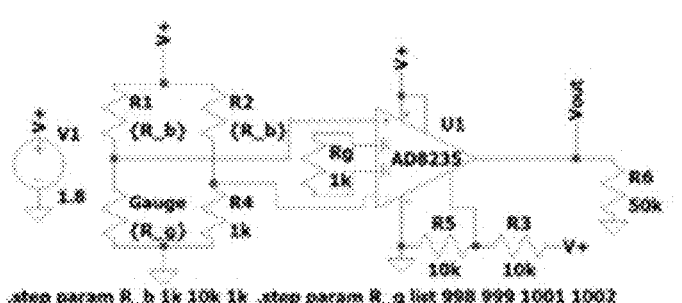
Figure 14D:
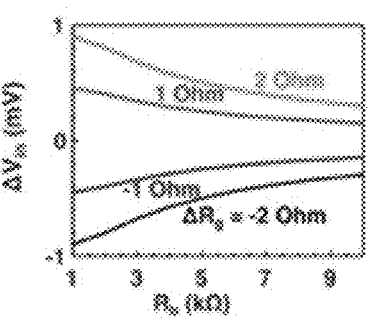
Figure 14E:
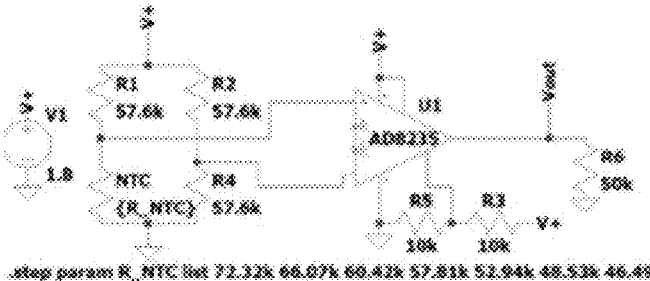
Figure 14F:
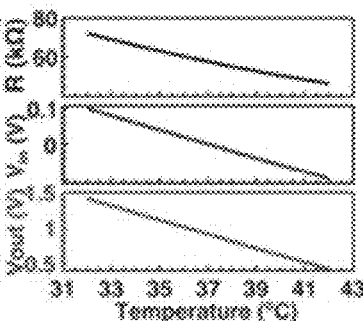
Figure 15A:
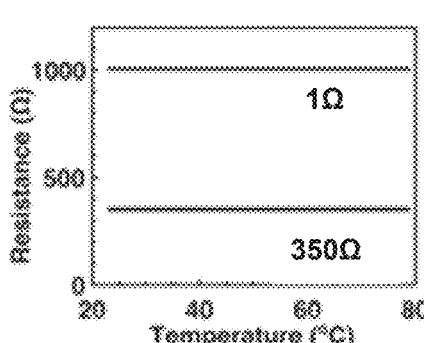
Figure 15B:
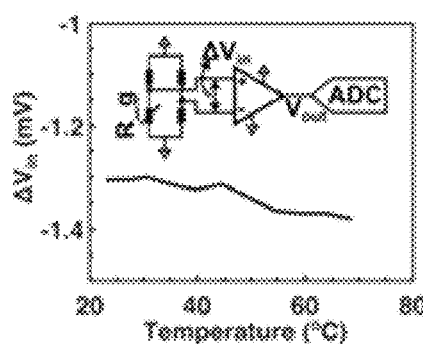
Figure 15C:
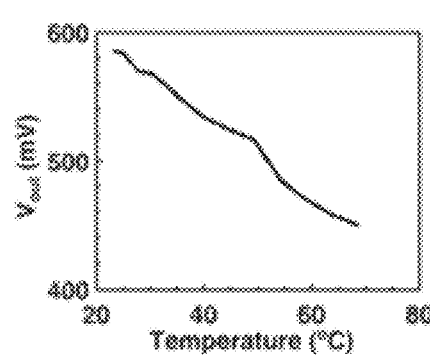
Figure 15D:
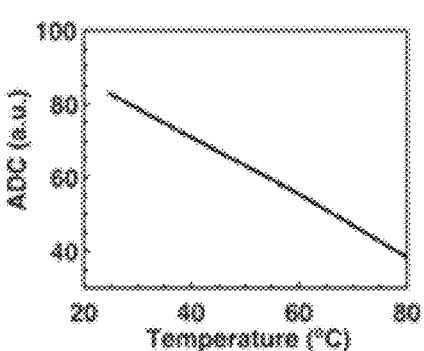
Figure 16A:
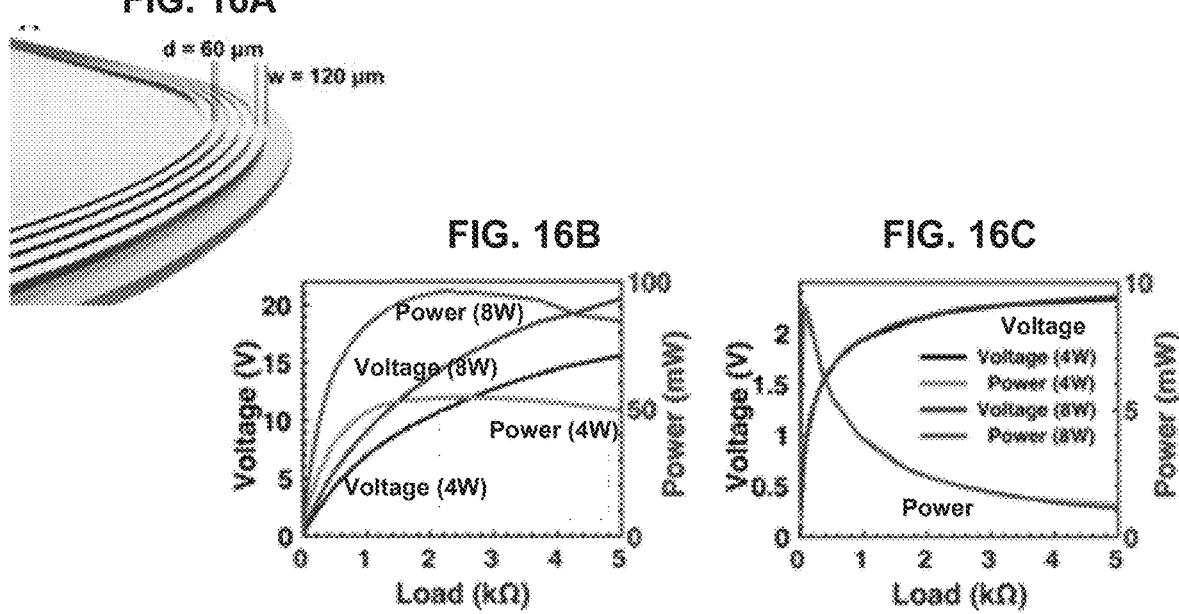

Circuit Simulation: LTspice XVII was utilized to simulate the electrical characteristics of the strain sensing and temperature sensing analog front-ends. The circuit diagram and choice of components are shown in FIG. 9. The output voltage of the Wheatstone bridge and instrumentation amplifier were selected as the output parameters. To simulate the basic characteristics of the strain sensor circuit (FIG. 15A-15B), resistance of the strain gauge was varied sinusoidally from 999Ω to 1001Ω with a frequency of 20 Hz. To simulate the strain sensing performance with various values of the bridge resistors ($R_b$) (FIG. 15C-15D), $R_b$ was varied linearly from 1 kΩ to 10 kΩ, at four values of the gauge resistance (998Ω, 999Ω, 1001Ω, and 1002Ω). To simulate the basic characteristics of the temperature sensing circuit, the thermistor resistance was varied from 72.32 kΩ to 46.49 k0 corresponding to the temperature range of 32° C.-42° C.

Device Characterization: Wireless power harvesting capability: radiofrequency (RF) power in the range of 2-8 W was provided by a long-range radio-frequency identification (RFID) reader module (Feig Electronic GmbH, ID ISC.LRM2500-A). The TX antenna was connected to a tuning/matching circuit board and tuned at 13.56 MHz with a voltage standing wave ratio (VSWR) below 1.5. A 1-turn circular TX antenna with diameter of 20 cm was used to power the devices for large animals, while the devices for rodents were powered by two types of TX antennas: a 45 cm×12 cm, 2-turn (at heights of 3 cm and 6 cm) coil that encloses the rat treadmill cage, and a 26 cm×33 cm, 2-turn (at heights of 3 cm and 9 cm) coil that encloses the rat home cage.

The completed wireless power harvesting module was tuned to 13.56 MHz and placed at the center of the test area in parallel with the floor. The rectified voltage was then recorded with a digital multimeter while the electrical load was varied from ~50Ω to ~5 kΩ. The spatial distribution of harvested power was measured at a fixed load (300Ω or 900Ω) while the device was placed at various locations and different heights (3 cm and 6 cm) in the test area. The angular dependence of the power harvesting capability was measured by varying the angle of the device with respect to the floor from 0 to 70° using a rotational jig. The dependence of harvested power on curvature radius was measured by conforming the device to curved surfaces of 3D printed objects with varying radii of curvature (1.6 cm-3.2 cm).

Wireless data communication: Wireless data reading was accomplished by ISOStart (V10.09.00, Feig Electronic GmbH). In order to mimic the in-vivo environment, the device was placed at the bottom of a 250 ml beaker filled with 1×PBS (Sigma Aldrich) solution. For the large animal device, data rate was measured while the handheld TX antenna was held at various heights from the device. For the rodent device, data rate was measured at representative locations in the test areas. Long-term data recording was performed using the rodent device and the 45 cm×12 cm TX antenna over a ~42-hour period while the device was immersed in PBS solution and constantly moving back-and-forth (25 cm/s) on a custom-built rat treadmill. A custom-built thermometer (LMT70, Texas Instruments) was used to monitor the environment temperature.

Characterization of the wireless strain sensor: Bench-top tests of the wireless strain sensor were performed using an explanted sheep's femur. The periosteum of the mid-diaphysis was removed from the femur, and the metal foil strain gauge (N2A-06-S5182N-10C/E4, Micro-Measurements) of the wireless osseosurface system was attached to the femur using a cyanoacrylate-based adhesive (M-Bond 200, Micro-Measurements). A wired strain gauge was subsequently bonded on top of the wireless gauge following the same procedure using a stereomicroscope to ensure overlap and alignment of the sensing elements. The sheep femur was loaded in four-point bending using a servo-hydraulic materials testing system (Series 810, MTS Systems Corporation) while recording load and strain from the wired sensors using a standard data acquisition system (System 8000 and StrainSmart, Micro-Measurements). Measurements from the wireless gauge were recorded with a handheld antenna using the Feig reader and ISOStart. Various load profiles were tested, including a linear ramp load, and cyclic loading with a sinusoidal wave pattern, a square wave pattern and a triangle wave pattern. The femur was loaded to a peak load of 190 kg at rates ranging from 5-60 kg/sec in each test.

Characterization of the wireless optical stimulation module: The current-voltage (I-V) characteristics of the μ-ILED was recorded with a source measurement unit (SMU, Keithley 2450) operating in the linear sweeping mode. The optical power was measured with an integration sphere (OceanOptics FOIS-1). The current consumption of the μ-ILED was measured by a customized circuit where a 10Ω resistor and a MOSFET (PMZ130UNE, Nexperia) were connected in series with the μ-ILED and a microcontroller (ATTiny 13A, Microchip Technology) was used to switch the MOSFET on and off with pre-defined frequencies and duty cycles. The circuit was powered by a direct current (DC) power supply (1.8 V) while an Oscilloscope (Siglent SDS 1202X-E) was used to record the voltages across the 10Ω shunt resistor from which the current could be calculated.

Characterization of the wireless thermography. The wireless temperature sensor was immersed in a water bath whose temperature was varied from 33 to 41° C. using a hotplate and monitored by a commercial thermocouple digital thermometer. The sensor signal was wirelessly recorded with a handheld antenna using the Feig reader and ISOStart, and used for sensor calibration.

Figures 20A, 20B, 21A, 21B, 21C, 21D:
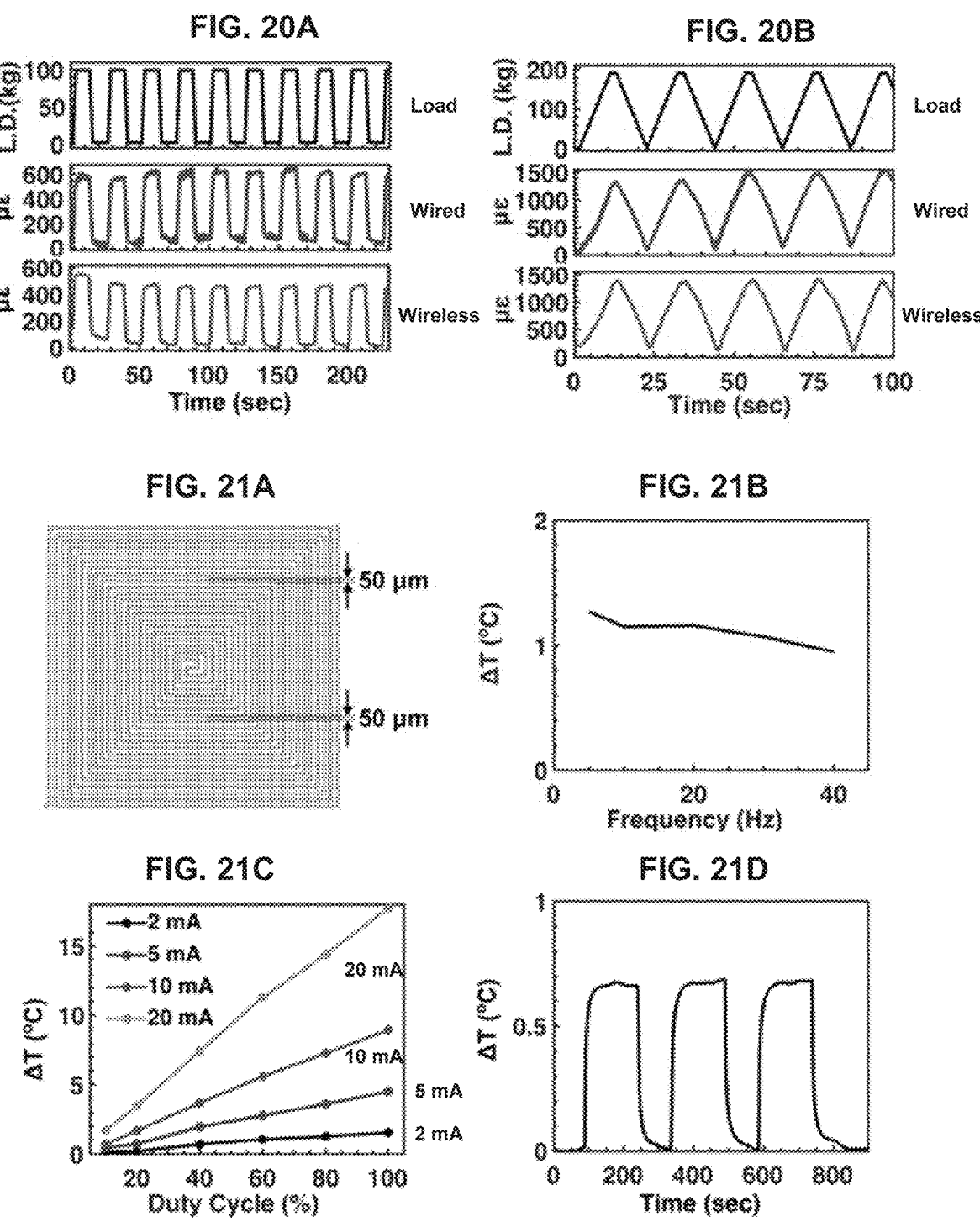

In order to characterize the resolution of the wireless thermographic biointerface, the copper (Cu) on the bottom side of the Pyralux substrate was laser ablated to form a micro-heater beneath the NTC thermistor (design of the micro-heater is shown in FIG. 21A). The micro-heater was powered by the rectified voltage with a MOSFET as a switch that was controlled by a microcontroller with a duty cycle varying from 2% to 20%. The circuit was immersed in a water bath and a handheld antenna was used to wirelessly power the micro-heater and retrieve the sensor signal. The resolution of the temperature sensor was subsequently determined by the smallest sensor response that could be distinguished from the background noise.

A circuit with co-located NTC thermistor and μ-ILED (~0.1 mm apart) was fabricated and used to demonstrate the capability to directly measure the thermal impacts of optical stimulation. The thermistor and μ-ILED were immersed in a PBS bath to mimic the in-vivo environments and to prevent the device from overheating at high optical power. A function generator (Siglent, SDG 1032X) was used to drive the μ-ILED with varying voltage (1.85 V, 2 V and 2.12 V), frequency (5-40 Hz) and duty cycle (5-80%), while the sensor signal was wirelessly read out with a handheld antenna.

Mechanical durability of serpentine interconnects: The serpentine interconnects were mounted on a custom-built stretching stage and subjected to ~250% strain and stretched cyclically for 10,000 cycles. The resistance of the serpentine copper traces was measured with a digital multimeter.

The strain gauge of an osseosurface electronic system was bonded onto a piece of Kapton foil (~75 µm thick). The Kapton foil was mounted on the stretching stage and subjected to cyclic bending with a radius of curvature of ~2 cm while the serpentine interconnects were stretched to various lengths (ΔL~3 cm and 5 cm) with a separate stage. The strain sensor signal was wirelessly recorded with a circular TX antenna (20 cm in diameter). The same measurement was repeated after the serpentine had been stretched for 5,000 cycles and 10,000 cycles.

Mechanical simulation: Ansys® 2019 R2 Static Structural was utilized for static-structural Finite Element Analysis (FEA) simulations to study the strains induced in the Cu traces of the serpentine interconnects, and the effectiveness of mechanically isolating the strain gauge from other parts of the device. The components of the devices, including the copper and constantan traces, Pb-free solder, polyimide (PI), and parylene encapsulation layers, were modeled using the layouts used in device design. The mechanical properties (Young's Modulus (E) and Poisson's Ratio (v)) used for the simulation were: $E_{PI}$=4 GPa, $v_{PI}$=0.34; $E_{Cu}$=121 GPa, $v_{Cu}$=0.34; $E_{Constantan}$=162 GPa, $v_{Constantan}$=0.32; $E_{Parylene}$=2.7579 GPa, $v_{Parylene}$=0.4; $E_{solder}$=43 GPa, $v_{solder}$=0.29.

Simulation of strain in serpentine interconnects: The model was simulated using the following meshing parameters: Program Controlled Nonlinear Mechanical Elements with an Element Size of $8.0\times10^{-5}$ m, a Body Sizing insert condition with Element Size $1.0\times10^{-5}$ m applied to all the traces, and a Body Sizing insert condition with Element Size $2.0\times10^{-5}$ m applied to the PI layer. The simulation was performed by fixing one end of the selected serpentine segment and applying a displacement of 5.75 mm upwards to the other, producing a deformation replicating that observed in bench top testing of the serpentine interconnects (FIG. 5B).

Mechanical isolation of the strain gauge: The model was simulated using the following meshing parameters: Program Controlled Mechanical Elements with an element resolution of 2, and a Body Sizing insert condition with Element Size $2.0\times10^{-5}$ m applied to all the traces. Two simulations were performed, both with 1000µε applied to the bone model by fixing one end while displacing the other end by 7.9×10–6 m, as shown in FIG. 22B: i.) no strain was applied to the serpentine interconnects; ii.) the serpentine interconnects were subjected to 3D displacements (x: 1 mm, y: 3 mm, and z: 3 mm. Details in FIG. 22B).

Animal Studies: All animal experiments were performed following an IACUC approved protocol.

In-vivo study in rats: Five male 450-gram Sprague Dawley rats were used. The implanted devices were sterilized using ethylene oxide and aerated for 24 hours prior to placement. Rats were anesthetized using isoflurane and were given a subcutaneous injection of 1.0 mg/kg Buprenorphine SR prior to surgery. A 2 cm incision was made along the midline of the back over the lumbar spine. A 1 cm incision was made over the lateral thigh, and the anterior surface of the femur was exposed subperiosteally through a lateral approach. The device was placed in a subcutaneous location through the back. Passage of the strain gauge (i.e., the sensor gauge (110)) into the thigh via a subcutaneous tunnel was facilitated by the serpentine interconnect. The strain gauge (i.e., the sensor gauge (110)) was fixed to the femur using a cyanoacrylate adhesive (M-Bond 200, Micro-Measurements). Layered closure was performed using 5-0 vicryl for fascia and 4-0 Quill for subcutaneous tissues prior to recovery from anesthesia.

Figures 6A, 6B, 6C, 6D, 6E, 7A, 7B, 7C:
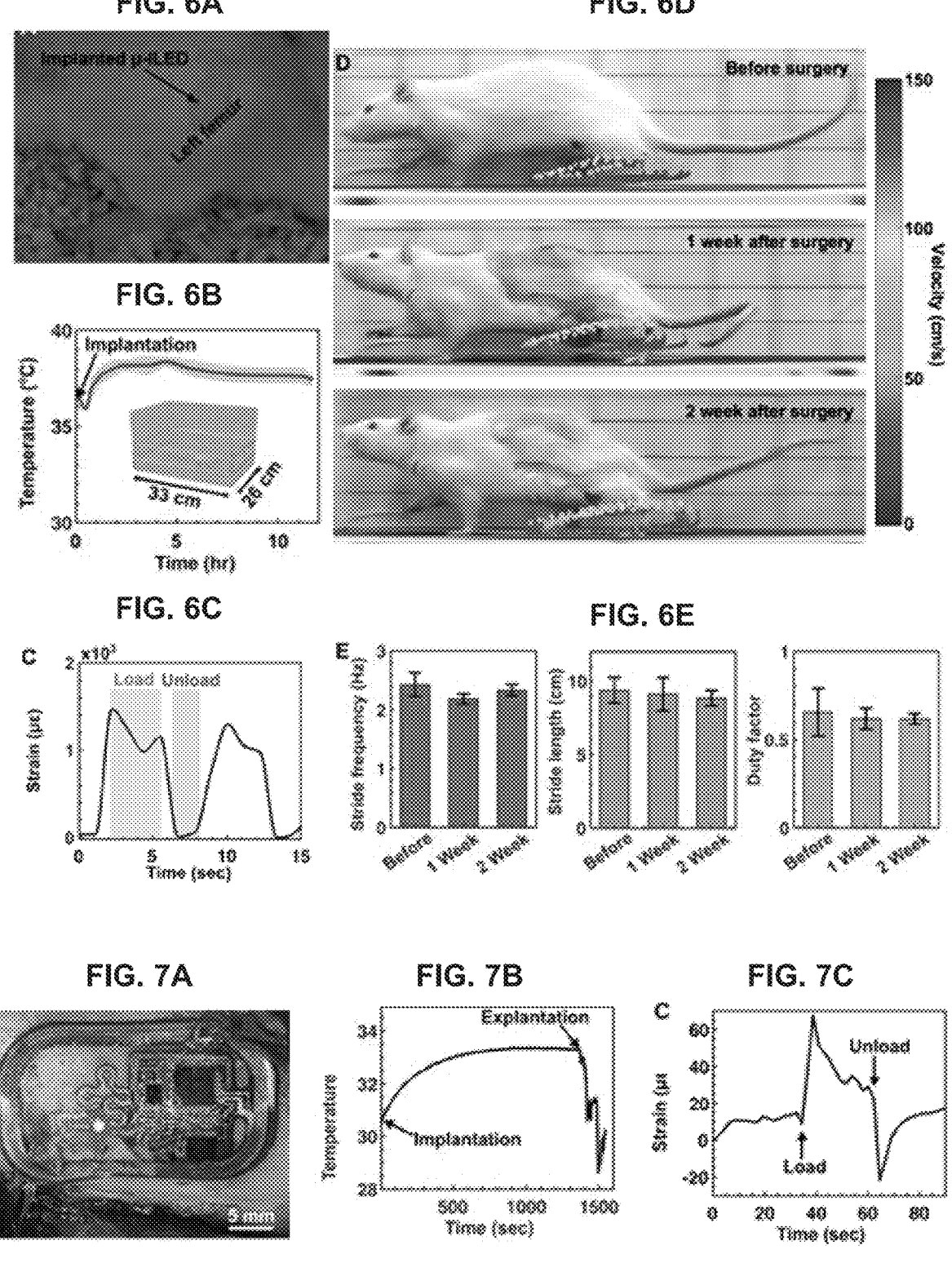

During recovery, strain and temperature measurements were continuously recorded with the 26 cm×33 cm TX antenna while rat behavior was recorded via a webcam. After 2 days, measurements were collected while rats walked on a custom-built treadmill at 25 cm/s. Sensor signals were recorded wirelessly with the 45 cm×12 cm TX antenna while high speed (1920×1080, 120 frame per second, iPhone 6S) videos were recorded with a camera placed ~50 cm from the treadmill for the purpose of deep neural network of the gait. Before each exercise session, the rat received a minimum of 20 min of habituation to the treadmill. Strain changes were observed during loading and unloading of the femur (FIG. 6C). After 2 weeks the rats were euthanized. Following euthanasia device placement was characterized by scanning rats at 20 µm resolution using a Siemens Inveon micro-CT Scanner. For histology, tissue surrounding the implanted device was excised, fixed in 10% formaldehyde for 24 hours and embedded in paraffin. Ten-micron sections were cut and stained with hematoxylin and eosin. Slides were viewed using a Nikon microscope coupled to a Nikon DS-Fi1 camera at magnifications ranging from 20-100.

In-Situ study in sheep: One male 2.5-year-old sheep was used to confirm function of the device in a large animal. The sheep was a control used in another study and had a 4.2 cm femoral defect created 6 months prior to use. Device placement occurred following administration of euthanasia medications for the other study and was completed prior to significant changes in body temperature. The anterior surface of the mid-diaphyseal humerus was exposed subperiosteally through a lateral approach. The wireless device was fixed to the anterior surface of the humerus deep to brachialis. The facia and skin were closed with running sutures. Measurements of strain and temperature were collected continuously using a handheld antenna placed on the skin for 20 minutes following surgical placement of the device. Function of the strain sensor was confirmed by loading the sheep's humerus in three-point bending (FIG. 7C).

Deep neural network analysis: DeepLabCut (version 2.2.b6) was used to perform deep neural network analysis. The neural net was trained with a 1-min video clip where 200 frames were extracted as training material. The training session was performed with 200,000 iterations on the High-Performance Computer of University of Arizona. After training, a 3-second video clip with consistent gait was tracked and analyzed by the software to extract the coordinates of the left hind paw for each frame. The timestamp and coordinates were subsequently utilized to calculate the spatiotemporal gait characteristics, including stride length, stride frequency, duty factor, and the velocity of the paw.

Osseosurface electronics bone attachment: An applicator comprised of a 3D-printed frame and an elastomeric membrane (details in FIG. 10) was utilized to facilitate fast attachment of the device on the bone surface. Before attaching the device, the surface of the bone was abraded. The device was first attached to the applicator with the top side in contact with the elastomeric membrane. Cyanoacrylate adhesive (M-Bond 200, Micro-Measurements) was then applied to the bottom side of the micro-device. The applicator was subsequently placed on the bone and pressed gently against the bone in order to conform the device to the bone surface.

Next, the device was firmly pressed against the bone with an even force until the adhesive cured. Finally, the applicator was carefully peeled off with minimal out-of-plane shear force between the membrane.

Device operation in deep tissue: Slits of ~3 cm length were cut into the porcine tissues (2 pieces stacked together, 4 cm thick each, FIG. 12) at various thicknesses. The rectified voltage and data rate were recorded with a handheld TX antenna while the device was loaded with 1 Ωk and inserted into the slits at each thickness.

Real-time data visualization through tissues: A device was attached on a sheep's humerus following the device attachment procedures described above, and subsequently covered by a piece of porcine skin (~1 cm thick). An NFC-enabled smartphone running custom software was brought in proximity to the porcine skin. The NFC connection was subsequently established, and the sensor signals were visualized on the smartphone in real time. To demonstrate real time readout, a device was attached onto a model of a human femur, then covered with a piece of porcine skin, and subsequently operated through the tissue with a smartphone while the femur model was strained to induce signal change.

Devise design: The creation of osseosurface electronics requires several technical innovations to enable a device footprint and mechanical properties suitable for direct attachment onto the bone surface to minimize mechanical mismatch with the surrounding tissues, and electromagnetic design allowing direct readout through thick tissues with portable devices to enable smart therapeutics. FIG. 2B shows a device that meets these design criteria (2.5 cm×1.5 cm, ~170 mg) and enables direct, conforming attachment to the curved osseosurface with minimal impact on the surrounding tissues. The device features mechanically isolated biointerfaces that are capable of measuring deformation of the bone with microstrain accuracy, high fidelity thermography with mK resolution and photonic stimulation capabilities. The system features a hybrid integration of mechanical compliant flexible substrate with high-performance analog and digital functionalities provided by miniaturized off-the-shelf components arranged in a configuration that enables conformality and reliable operation when applied to the curvilinear surface of the bone, as depicted by the layered device makeup shown in FIG. 2C. Details of the device fabrication and list of components are provided in the methods described herein and FIG. 9. The inset of FIG. 2C highlights the multifunctional biointerface comprised of a metal-foil strain gauge, a negative temperature coefficient (NTC) thermistor and a microscale inorganic light-emitting diode (μ-ILED), enabling simultaneous recording of local biophysical signals and on-demand delivery of exogenous stimulation. The device geometry is highly adaptable to accommodate a range of implementation scenarios and anatomic structure. FIG. 2D shows a device variant applied to a sheep humerus, a testbed to gain insight on capabilities for use as a diagnostic tool after recovery from surgery. Device designs were also developed for exploratory research in small animal models.

FIG. 2E describes the electrical working principle of the system that enables wireless, battery-free operation in a form factor suitable for full implantation. Near-field magnetic resonant coupling (13.56 MHz, specific absorption rate (SAR) <20 mW/kg) between an external primary loop antenna (TX antenna) and the on-board loop antenna (RX antenna) enables, for the first time, reliable power harvesting through thick tissues (>10 cm) with hardware that is compatible with NFC protocols widely available in portable devices. Optimized harvesting electronics matched to digital and analog electronics provide power to an NFC system-on-chip (SoC) that enables operational control through a microcontroller (MCU) and NFC transponder in a compact package (4 mm×4 mm), and analog front-ends (AFE) comprised of passive filters and instrumentation amplifiers that read out thermographic and strain sensors. Design of the sensing circuits is facilitated by circuit simulation (details in the methods described herein), yielding a strain sensing AFE that consumes 3.24 mW with a sensitivity of 0.194 mV/με, and a thermography AFE that consumes <0.06 mW with a sensitivity of 98.9 mV/° C. (FIG. 14A-14F). Digital engineering and manufacturing enable rapid development and deployment of osseosurface electronics in form factors suitable for a variety of operational conditions. FIG. 2F shows an example of a system variant that enables operation in a freely moving small animal model without tethers or other externalized elements, which allow advanced exploratory studies. The ultrathin mechanics and low displacement volume (<0.2 cm$^3$) of the device enable rapid recovery of the subject from surgical placement and high-fidelity behavioral studies while collecting bioinformation in real time which is not possible with existing wire bound technologies.

System Characteristics: Consistent operation of osseosurface electronics relies on robust wireless power transfer through tissues for large animal models and for therapeutic applications. In the case of small animal models for exploratory research free motion in a variety of test arenas is required. Both scenarios required robust power transfer and efficient wireless power transfer via magnetic resonant coupling that can be boosted by adopting an RX antenna with high quality factor (Q-factor), in this case antennas with high inductance and low impedance. FIG. 3A displays a large animal model device with an RX antenna (3 turns, 600 μm wide, 60 μm spacing) optimized for operational voltages of 2.5 V, a limitation introduced by the CMOS (complementary metal-oxide-semiconductor) technology used by the NFC SoC (details in FIGS. 16A-16C and 17A-17H). As shown by the power harvesting characteristics (FIG. 3B) measured at the center of a handheld TX antenna (diameter ~20 cm), the maximum values of harvested power (~14 mW) and rectified voltage (~2.1 V) support operation at an electrical load of ~300Ω. Circular symmetry of the handheld TX antenna (2-8 W TX power) results in minimal spatial variation in harvested power (FIG. 3C and FIG. 18A-18F) in close proximity to the antenna and at a physiologically relevant distance (5 cm) that corresponds to the depth of implantation on a sheep or human humerus.

Figures 18A, 18B, 18C, 18D, 18E, 18F, 19A, 19B:
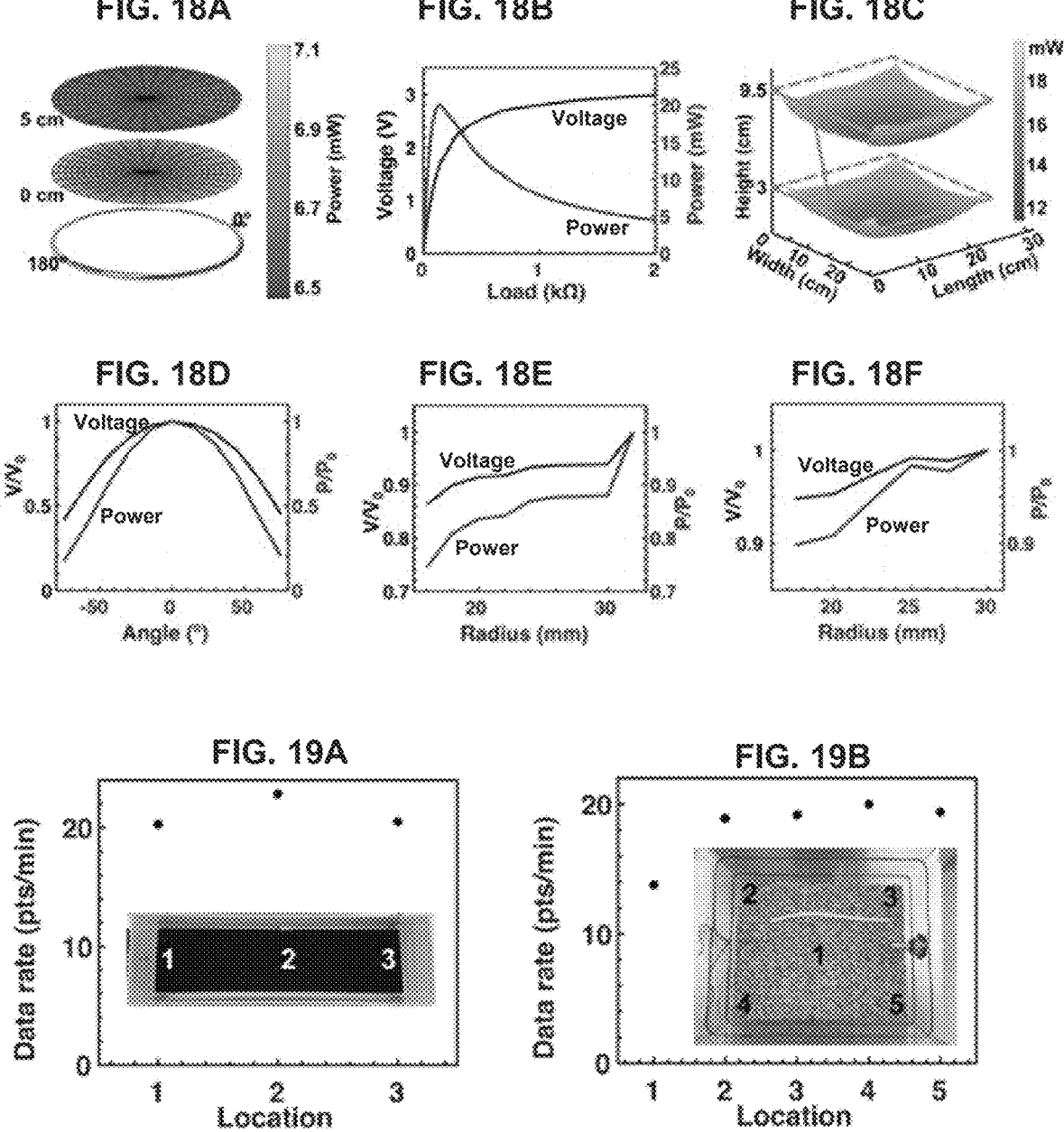

To provide power to freely moving small animals, critical for exploratory research in large test arenas (treadmill cage, 45 cm×12 cm; home cage, 26 cm×33 cm), devices designed for rat models (FIG. 3D) require an enlarged RX antenna (3.5 cm×2.5 cm) and device layout that features serpentine interconnects (~11 cm at full extension) to route the biointerface from the back of the subjects which houses the electronics and antenna section of the device to the limb that is the sensing target in the present experiments. Computational electromagnetic design enables harvesting performance of a rectified voltage of ~2.2 V at a load of 3000 (16.13 mW) at the center of the 45 cm×12 cm cage, providing a margin of 0.4 V to enable constant system voltage of 1.8V throughout all experimental conditions. The spatial distribution (FIG. 3F) of the harvested power in the 45 cm×12 cm cage exhibits sufficient power harvesting at two physiologically relevant heights, i.e. 3 cm and 6 cm that mark the lower and upper position limits during regular gait. Similar results are obtained for the 26 cm×33 cm TX antenna, revealing a rectified voltage of ~2.1 V at a load of 3000 (14.7 mW) at the cage center and sufficient power at physiologically relevant heights (FIGS. 18B and 18C).

A comparison between the power harvesting capability and the power consumption of the biointerface provides a practical guide for feasible in-vivo operation modes. FIG. 3G shows system power consumption, specifically ~3.24 mW in sensing mode, and ~10.26 mW as optical stimulation is activated, which represents ~60% and ~50% of the harvested power at the corresponding electrical loads, i.e. 900Ω and 300Ω, respectively (FIG. 3E). Considering the dependence of power harvesting capabilities on tilt angle and bending curvature radius (FIG. 18D-18F), stable and sufficient power can be guaranteed as long as the tilt angle is below 50° and curvature radius is above ~1 cm.

Wireless communication is crucial for implantable devices and often limits device operation in thick tissues. Benchtop experiments reflecting this scenario reveal that the device designed for deep tissue implantation immersed in PBS solution supports a nearly constant data rate of ~46 points/sec with a reading distance up to 7.5 cm from the handheld TX antenna (FIG. 3H) enabling operation as a diagnostic device in large animal models and human subjects. Similar tests designed for use in rodent models reveal uniform data rates in tests with rats in treadmill cages and home cages (FIGS. 19A and 19B). Long-term data recording (FIG. 3I) tests performed in the biologically relevant settings with a moving osseosurface electronic devices, (details in the methods described herein) results in stable communication over extended periods of time (42 hours, no limitation in operation time) where the recorded temperature profile matches that of environment temperature measured by a spatially separate thermometer.

Biointerface characterization: Characterization of the multimodal biointerface is performed with benchtop experiments that reflect the in vivo environment. Wireless strain sensors exhibit sensing performance on par with the gold standard wired strain measurement systems in typical physiologically relevant range (0-1200με), as confirmed by ramping and cyclic loading tests performed on a sheep bone specimen (FIGS. 4A, 4B, and 4C, details in methods described herein), with an estimated sensitivity of ~3.5 ADC/με and a resolution of ~14.3με. Repeatable, hysteresis-free response is obtained upon progressively increasing loads (FIG. 4B), indicating that a stable bond is formed between the strain gauge and the bone specimen. Reliability of the wireless strain sensor is further demonstrated by cyclic loading with sinusoidal (FIG. 4C), square and triangle (FIGS. 20A and 20B) wave forms.

Current implantable biointerfaces for the musculoskeletal system are typically limited to wired strain sensing, however the present device architecture offers the multimodal integration of stimulation capabilities currently only available in tethered embodiments. To demonstrate the feasibility of optical stimulation on an osseosurface electronic platform, miniaturized individually addressable μ-ILEDs were used to deliver stimulation to the bone and the surrounding tissue. The bone-tissue interface provides a unique platform capable of versatile optical coupling modes tailored for various application scenarios, such as phototherapeutic stimulation for bone regeneration and optogenetic activation of muscular contraction. FIG. 4D demonstrates this design flexibility with devices that are capable of illuminating the soft tissue side (left), bone side (middle), and multimodal stimulation (right). Typical operation for optical stimulation covers a parameter space of 5-20 Hz for applications such as sustained tetanic contraction, which is achieved on the present platform by utilizing a microcontroller for precisely controlled timing as demonstrated in FIG. 4E. The μ-ILEDs were used to create an ultra miniaturized form factor (240 μm×240 μm×100 μm) and high energy efficiency (>20%, FIG. 4F), ensure minimal thermal impact to the tissues.

Continuous monitoring of the local temperature can simultaneously be achieved on the present platform with a miniaturized (0201, 0.6 mm×0.3 mm) NTC thermistor that is integrated monolithically on the biointerface. The wireless temperature sensor exhibits linear response in physiologically relevant temperature ranges (33-41° C.) with a sensitivity of ~1920 ADC/K and a resolution of 10 mK (FIGS. 4G and 4H, details in the methods described herein), and can be used to monitor physiological events or to directly assess thermal impact of the μ-ILED, enabling closed loop control for phototherapeutic and stimulation applications requiring deep tissue penetration. FIG. 4I presents the thermal impact of the -ILED operating at increasing intensities (30-170 mW/mm$^2$) and duty cycles (5-80%) in a physiologically relevant environment mapping the parameter space for optogenetic stimulation and phototherapy. Experimental measurements are in agreement with FEA simulation enabling computational design of the interface. Irradiation that can be delivered by the present platform (e.g. 30 mW/mm$^2$) is well beyond the intensity used for optogenetic activation of skeletal muscles and evokes only a 0.29° C. temperature increase at a duty cycle of 80%. This suggests operation over a wide range of conditions without thermal activation of neuronal function.

Mechanical characterization: Subdermal implantation in small animal models involves placement in highly mobile areas which require a mechanical design strategy that can withstand repeated strain cycles. This is evident when studying the micro-CT scan (FIG. 5A) of a rat with an implanted osseosurface electronic device, where the device body is anchored subdermally around the lumbar vertebra and connection to the biointerface, which is located on the left femur. The solution to this is accomplished via self-similar serpentine interconnects. The durability of the serpentine interconnect is critically important for reliable in vivo operation. FEA simulation guided design enables reliable performance under repeated strains of over 250% while maintaining a maximum strain of ~0.7% in the Cu traces which is below 1%, the failure strain of Cu (FIG. 5B). Chronic stability is confirmed by cyclic straining to 250% for 10,000 cycles, with negligible change in conductivity (FIG. 5C). The biointerface is mechanically isolated by the serpentine interconnects, as confirmed by FEA (FIG. 5D) showing that stretching the serpentine by 250% does not influence the sensitivity or accuracy of the strain gauge, which is further validated by bench-top tests (FIGS. 5E and 5F and FIG. 13, details in the method described herein).

In-vivo studies in rodents: The subdermally implantable form factor and wireless, battery-free operation enable an in vivo multimodal bi-directional interface with the musculoskeletal system without compromising the free motion of subjects in various test situations (FIG. 6A-6E). The implantation of osseosurface electronics in rats involves a skin incision on the back of the subject, device placement into the subcutaneous space, subcutaneously tunneling the biointerface to the limb, attaching the biointerface to the femur with cyanoacrylate, and closing the skin with resorbable sutures (details in the methods described and FIG. 11). The optoelectronic interface attached on the bone surface allows direct optical stimulation of skeletal muscles in freely-moving subjects, as shown in FIG. 6A where illumination of the muscle is visually validated. This highlights a systematic advantage over traditional transdermal light sources or optical fiber-based techniques which are challenging to implement in highly mobile areas. In vivo device operation over extended time periods is demonstrated by thermographic recording over 11 hours in the home cage (FIG. 6B) following the surgical implantation of the device. A dip in local body temperature during the first half hour of recovery after implantation is observed which is expected hypothermia in response to isoflurane anesthesia and transfer from a warmed surgical table to a cooler recovery area. Following recovery from anesthesia the limb temperature remained within the published range of normal body temperature for male Sprague Dawley rats. Strain profile recorded wirelessly while on a custom treadmill with the 45 cm×12 cm TX antenna revealed characteristic loading and unloading phases with absolute strain values comparable to literature values for the rat femur obtained by tethered sensors.

Behavioral assays, such as gait analysis in particular, are useful tools to investigate pathogenesis and develop new therapeutics for musculoskeletal disorders such as osteoarthritis. Therefore, a basic requirement is that investigative devices not alter gait performance of the subjects, which is not easily achieved with tethered approaches. Due to the low-profile and mechanical compliance, osseosurface electronic implants do not affect the subject's gait, as revealed by deep neural network analysis of rats with implants (FIGS. 6D and 6E, details described herein). The heat maps displayed in FIG. 6D indicates that the trajectories of the paws of naïve (control) and experimental subjects with implants remain qualitatively the same and the spatial distribution of paw velocity is unchanged at various stages of the study. Spatiotemporal gait characteristics, including stride frequency, stride length and duty factor, presented in FIG. 6E, provide quantitative evidence that normal gait is sustained after implanting the osseosurface electronic device. The welfare of the test animals is also reflected by the steady weight-gain from two days post-surgery until the study is terminated (FIG. 23). In addition, histological analysis shows that the implant is surrounded by a thin layer of fibrous tissue containing blood vessels without evidence of inflammation or significant foreign body response after two weeks of in vivo operation (FIG. 24).

In-situ studies in large animal models. The scalability of the present platform enables its use in large animal models with minimal modifications. In situ operation of devices designed for large animals have been demonstrated on sheep humeri where the small footprint and soft mechanics of the device enable conformal attachment to the bone surface (FIG. 7A and FIG. 25A-25B). The thermography function allows for continuous monitoring of local temperature as an important indicator of the subject's health throughout the surgical procedure. As shown in FIG. 7B distinct features can be identified and correlated to events such as closing and re-opening of the incision. Devices implanted deep (>5 cm) in the body are warmed significantly faster to a saturation level close to the core body temperature than those implanted shallower (~2 cm). The wireless strain recording capability through thick tissues is validated while the humerus is loaded in 3-point bending (FIG. 7C), successfully capturing the bending events with well-discernable loading and unloading phases despite considerably lower strain than those measured during gait observed in sheep.

Wide dissemination of osseosurface electronics requires an implementation strategy that can be easily integrated into existing orthopedic surgical procedures. The present invention also demonstrates a device attachment strategy that is assisted by a 3D printed applicator and can be accomplished within ten minutes, minimally altering existing surgical protocols (FIG. 7D, details described herein). The applicator can be customized to match localized anatomic structure and device dimensions (FIG. 10), minimizing the impacts on the surrounding tissues and providing a path towards implementation as a diagnostic tool following routine surgical procedures.

Easy readout with industry standard RF protocols and rapid attachment with chronic interfaces enable osseosurface electronics to provide significant opportunities for the direct measurement of crucial indicators of bone health in real time. Consequently, this allows a point-of-care solution to monitoring post-fracture rehabilitation and managing musculoskeletal conditions. Here, the present invention demonstrates the successful device operation using an NFC-enabled smartphone through tissues, as shown in FIG. 7E where the sensor signals from a device covered by a piece of porcine skin (~1 cm thick) simulated human tissue on the tibia are directly visualized in real time as the smartphone is used to provide power to and wirelessly communicate with the device. These results demonstrate the feasibility of operating osseosurface electronics with a smartphone in an at-home setting. Locations covered with several muscle layers such as the femur, can be accessed with a dedicated reader solution. FIG. 7F plots the relative data rate and harvested power as functions of tissue thickness between the reader and the device, showing no degradation in either data rate or available power level at the devices at tissue thickness up to 11.5 cm. This highlights successful wireless power transmission and data communication with a battery-free and soft implantable device through thick tissues, which enables implantation in almost any location on the human skeletal system.

The miniaturized form factors, soft mechanics, versatile sensing/stimulation options, as well as robust wireless power harvesting and communication capabilities make osseosurface electronics a powerful platform to establish direct and chronic bi-directional interface with the musculoskeletal system. This offers unprecedented opportunities for mechanistic studies of osteogenesis and pathogenesis of musculoskeletal diseases, as well as the development of new types of diagnostics and therapeutics.

As used herein, the term "about" refers to plus or minus 10% of the referenced number.

Although preferred embodiments of the present invention have been shown and described, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" and/or the phrase "comprised of" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An implantable sensor device (100) for monitoring of the musculoskeletal system, said implantable sensor device (100) comprising:

a) a strain gauge (110);

b) an analog front end (120) operatively coupled to the strain gauge (110), wherein the analog front end (120) amplifies information from the sensor;

c) a processor (130) operatively coupled to the analog front end (120), wherein the processor (130) digitalizes the information from the analog front end;

d) a radiofrequency (RF) transmitter (140) operatively coupled to the processor (130), wherein the RF transmitter sends information to an external reader (150); and e) an energy harvesting system (160) operatively coupled to the RF transmitter (140), wherein the energy harvesting system (160) harvests energy from the external reader (150);

wherein the implantable sensor device (100) is configured to be permanently attached to a bone surface via calcium ceramic particle coating, and wherein the strain gauge (110) is configured to interface with the bone surface and measures changes in bone strain.

2. The sensor device (100) of claim 1, further comprising a thermistor operatively coupled to the analog front end (120), wherein the thermistor is a negative temperature coefficient (NTC) thermistor.

3. The sensor device (100) of claim 1, further comprising a light emitting diode (LED) operatively coupled to the processor (130), wherein the LED is a microscale inorganic light-emitting diode.

4. The sensor device (100) of claim 1, wherein a biointerface of the sensor device (100) comprises the strain gauge (110), a thermistor and an LED.

5. The sensor device (100) of claim 4, wherein the biointerface enables simultaneous recording of local biophysical signals and on-demand delivery of exogenous stimulation, wherein the local biophysical signals comprise bone strain and/or local temperature, and wherein the exogenous stimulation comprises an optical stimulation to the bone and surrounding tissues.

6. The sensor device (100) of claim 1, wherein bone strain and/or load changes measured by the sensor gauge (110) are converted to electronic signals by the processor (130), and the electronic signals are transmitted by the RF transmitter (140) to the external reader (150).

7. The sensor device (100) of claim 1, wherein the external reader (150) is configured to be external to a body in which the sensor is implanted, wherein the external reader (150) is a smart device.

8. The sensor device (100) of claim 1, where the sensor device (100) is used to determine bone stiffness, determine the risk of a bone fracture, monitor arthrodesis, monitor fracture healing, diagnose osteoporosis, treat osteoporosis, or a combination thereof.

9. The sensor device (100) of claim 8, wherein the device (100) is used with other components to treat osteoporosis, wherein the other components comprise another implanted device that allows the release of chemicals or molecules that are known to induce new bone formation, wherein the chemicals or molecules known to induce new bone formation comprise TGF-beta 1, or BMP-2 or BMP-7 or a combination thereof.

* * * * *